(12) United States Patent
Varga et al.

(10) Patent No.: US 11,857,710 B2
(45) Date of Patent: Jan. 2, 2024

(54) VENTILATION MASK

(71) Applicant: SunMed Group Holdings, LLC, Grand Rapids, MI (US)

(72) Inventors: Christopher M. Varga, Laguna Hills, CA (US); Ryan G. Redford, Tucson, AZ (US); Dennis White, Yorba Linda, AZ (US); Thomas Dillingham, Aliso Viejo, CA (US)

(73) Assignee: SunMed Group Holdings, LLC, Grand Rapids, MI (US)

( * ) Notice: Subject to any disclaimer, the term of this patent is extended or adjusted under 35 U.S.C. 154(b) by 1043 days.

(21) Appl. No.: 16/526,876

(22) Filed: Jul. 30, 2019

(65) Prior Publication Data
US 2020/0038617 A1 Feb. 6, 2020

Related U.S. Application Data

(60) Provisional application No. 62/712,933, filed on Jul. 31, 2018, provisional application No. 62/773,820, filed on Nov. 30, 2018.

(51) Int. Cl.
*A61M 16/06* (2006.01)
*A61M 16/22* (2006.01)
(Continued)

(52) U.S. Cl.
CPC .......... *A61M 16/085* (2014.02); *A61B 5/082* (2013.01); *A61B 5/6803* (2013.01); *A61M 16/06* (2013.01);
(Continued)

(58) Field of Classification Search
CPC ..... A41D 13/1146; A61F 13/124; A61F 9/04; A61M 16/0051; A61M 16/009;
(Continued)

(56) References Cited

U.S. PATENT DOCUMENTS 2,675,803 A * 4/1954 Kaslow ................. A61M 16/06
128/206.28
2,859,748 A * 11/1958 Hudson ................. A61M 16/06
128/206.28
(Continued)

FOREIGN PATENT DOCUMENTS

CN 101014311 8/2007
CN 203235110 U 10/2013
(Continued)

OTHER PUBLICATIONS

International Search Report and Written Opinion for Application No. PCT/US2019/044213, dated Nov. 7, 2019, 20 pages.
(Continued)

*Primary Examiner* — Annette Dixon
(74) *Attorney, Agent, or Firm* — Sheridan Ross P.C.

(57) ABSTRACT

Ventilation masks are described herein. A ventilation mask includes a mask body and a gas manifold. The mask body defines a patient cavity and further includes a patient opening in fluid communication with the patient cavity; and at least one vent opening formed through the mask body, the at least one vent opening in fluid communication with the patient cavity, wherein the at least one vent opening is disposed generally opposite to the patient opening. The gas manifold is coupled to the mask body. The gas manifold can define a gas channel. The gas manifold can include a plurality of vectored gas ports in fluid communication with the gas channel, wherein the plurality of vectored gas ports are configured to create a curtain effect gas flow within the patient cavity to form a gas curtain within the patient cavity and adjacent to the at least one vent opening.

23 Claims, 16 Drawing Sheets

(51) Int. Cl.
  *A61M 16/08* (2006.01)
  *A61B 5/08* (2006.01)
  *A61B 5/00* (2006.01)

(52) U.S. Cl.
  CPC .... *A61M 16/0611* (2014.02); *A61M 16/0683* (2013.01); *A61M 16/22* (2013.01); *A61M 2202/0208* (2013.01); *A61M 2205/6081* (2013.01); *A61M 2230/43* (2013.01)

(58) Field of Classification Search
  CPC .... A61M 16/01; A61M 16/021; A61M 16/06; A61M 16/0666; A61M 16/0672; A61M 16/0683; A61M 16/0816; A61M 16/0833; A61M 16/085; A61M 16/101; A61M 16/107; A61M 2016/0024; A61M 2016/0661; A61M 2202/0208; A61M 2205/0216; A61M 2205/0227; A61M 2206/14; A61M 2210/0618; A61M 2230/432; A62B 23/025; A62B 27/00; Y10S 128/91
  See application file for complete search history.

(56) References Cited

U.S. PATENT DOCUMENTS

| | | | |
|---|---|---|---|
| 3,395,701 A * | 8/1968 | Bartlett, Jr. | A62B 27/00 128/204.22 |
| 4,201,205 A * | 5/1980 | Bartholomew | A61M 16/06 128/205.25 |
| 4,231,363 A * | 11/1980 | Grimes | A61M 16/06 128/206.28 |
| 4,248,218 A * | 2/1981 | Fischer | A61M 16/009 128/207.18 |
| 4,263,908 A | 4/1981 | Mizerak | |
| 4,354,488 A * | 10/1982 | Bartos | A61M 16/0672 128/205.25 |
| 4,454,880 A * | 6/1984 | Muto | A61M 16/0683 128/207.18 |
| 5,005,571 A * | 4/1991 | Dietz | A61M 16/06 128/207.18 |
| 5,012,805 A * | 5/1991 | Muckerheide | A41D 13/1146 128/205.28 |
| 5,183,059 A * | 2/1993 | Leonardi | A61F 9/04 128/858 |
| 5,400,781 A | 3/1995 | Davenport | |
| 5,474,060 A | 12/1995 | Evans | |
| 5,857,460 A * | 1/1999 | Popitz | A61M 16/085 128/204.22 |
| 6,357,437 B1 | 3/2002 | Jacques | |
| 6,418,928 B1 | 7/2002 | Bordewick et al. | |
| 6,450,166 B1 | 9/2002 | McDonald et al. | |
| 6,491,034 B1 | 12/2002 | Gunaratnam et al. | |
| 6,595,207 B1 | 7/2003 | McDonald et al. | |
| 6,631,719 B2 | 10/2003 | McDonald et al. | |
| 6,837,238 B2 | 1/2005 | McDonald | |
| 7,063,084 B2 | 6/2006 | McDonald | |
| 7,114,498 B1 | 10/2006 | Nashed | |
| 7,255,107 B1 * | 8/2007 | Gomez | A61M 16/0666 128/207.18 |
| 7,909,035 B2 | 3/2011 | Thornton | |
| 8,042,540 B2 | 10/2011 | McDonald et al. | |
| 8,336,549 B2 | 12/2012 | Nashed | |
| 8,365,734 B1 | 2/2013 | Lehman | |
| 8,826,909 B2 | 9/2014 | Nashed | |
| 8,960,195 B2 | 2/2015 | Lehman | |
| 9,010,330 B2 | 4/2015 | Barlow et al. | |
| 9,022,029 B2 | 5/2015 | Varga et al. | |
| 9,138,169 B2 | 9/2015 | Beard | |
| 9,272,108 B2 | 3/2016 | Hu | |
| 9,339,621 B2 | 5/2016 | McAuley et al. | |
| 9,399,106 B2 | 7/2016 | Borody | |
| 9,486,598 B2 | 11/2016 | Takatori et al. | |
| 9,775,541 B2 | 10/2017 | Inoue | |
| 9,884,160 B2 | 2/2018 | McAuley et al. | |
| 10,004,865 B2 | 6/2018 | McAuley et al. | |
| 10,058,672 B2 | 8/2018 | Matsubara et al. | |
| 10,065,011 B2 | 9/2018 | Matsubara et al. | |
| 10,188,818 B2 | 1/2019 | Bowsher | |
| 10,265,487 B2 | 4/2019 | Booth Wise et al. | |
| 2006/0081248 A1 | 4/2006 | McDonald | |
| 2009/0250061 A1 | 10/2009 | Marasigan | |
| 2011/0203591 A1 * | 8/2011 | Amarasinghe | A61M 16/06 128/205.25 |
| 2012/0132208 A1 | 5/2012 | Judson et al. | |
| 2012/0289851 A1 | 11/2012 | Varga et al. | |
| 2014/0238400 A1 | 8/2014 | Miller | |
| 2014/0366890 A1 | 12/2014 | Tao et al. | |
| 2015/0202473 A1 | 7/2015 | Curran et al. | |
| 2015/0209533 A1 | 7/2015 | Boussignac | |
| 2015/0217075 A1 | 8/2015 | Nair | |
| 2016/0030695 A1 | 2/2016 | Chang | |
| 2016/0271351 A1 | 9/2016 | Frater et al. | |
| 2017/0028154 A1 | 2/2017 | Takatori et al. | |
| 2017/0151406 A1 | 6/2017 | Booth Wise et al. | |
| 2017/0189635 A1 | 7/2017 | Beard | |
| 2017/0196512 A1 | 7/2017 | Inoue | |
| 2018/0043121 A1 | 2/2018 | Goulitski et al. | |
| 2018/0185601 A1 | 7/2018 | Koch | |
| 2018/0207386 A1 | 7/2018 | Kertser et al. | |
| 2018/0235511 A1 | 8/2018 | Kertser | |

FOREIGN PATENT DOCUMENTS

| | | |
|---|---|---|
| CN | 203591509 U | 5/2014 |
| CN | 105944211 | 9/2016 |
| CN | 106039517 A | 10/2016 |
| CN | 106659860 | 5/2017 |
| CN | 106912194 | 6/2017 |
| CN | 107224288 | 10/2017 |
| EP | 1095269 B1 | 5/2001 |
| EP | 1804875 B1 | 7/2007 |
| EP | 2015815 A4 | 1/2009 |
| EP | 2186539 B1 | 5/2010 |
| EP | 2319569 B1 | 5/2011 |
| EP | 2753392 B1 | 7/2014 |
| EP | 2859845 | 4/2015 |
| EP | 2890438 B1 | 7/2015 |
| EP | 2890463 B1 | 7/2015 |
| EP | 2903515 A1 | 8/2015 |
| EP | 3166675 | 5/2017 |
| GB | 2506621 | 4/2014 |
| JP | 6293760 B2 | 10/2015 |
| JP | 2016000157 A | 1/2016 |
| WO | WO-2007128100 A1 | 11/2007 |
| WO | WO-2012094730 | 7/2012 |
| WO | WO-2017131607 | 8/2017 |
| WO | WO-2018017565 | 1/2018 |
| WO | WO-2018029689 | 2/2018 |
| WO | WO-2018134821 | 7/2018 |
| WO | WO-2018150431 | 8/2018 |

OTHER PUBLICATIONS

English Translation of Official Action for China Patent Application No. 201980050699.3, dated Sep. 4, 2023 11 pages.

* cited by examiner

VENTILATION MASK

CROSS REFERENCE

This application claims priority from Provisional U.S. Application Ser. No. 62/773,820 filed on Nov. 30, 2018, and entitled VENTILATION MASK, and Provisional U.S. application Ser. No. 62/712,933 filed on Jul. 31, 2018, and entitled VENTILATION MASK.

FIELD OF THE INVENTION

The present disclosure generally relates to ventilation masks, and, in particular, to ventilation masks with vent openings.

BACKGROUND

Supplemental gas (e.g., air or oxygen) delivery to patients is a well-known treatment for a number of illnesses and conditions. For patients with respiratory difficulties, oxygen may be provided from an oxygen supply (e.g., pressurized cylinder, etc.) through a regulator and ventilation mask. A ventilation mask may include openings to permit medical procedures, eating, drinking, hygiene, and to prevent claustrophobia.

In some applications, the delivery of supplemental gas and/or the sampling of exhaled gas with a ventilation mask including openings may be difficult.

SUMMARY

The disclosed subject matter relates to ventilation masks with vent openings. In certain embodiments, a ventilation mask is disclosed that comprises a mask body defining a patient cavity, the mask body comprising: a patient opening in fluid communication with the patient cavity; and at least one vent opening formed through the mask body, the at least one vent opening in fluid communication with the patient cavity, wherein the at least one vent opening is disposed generally opposite to the patient opening; and a gas manifold coupled to the mask body, the gas manifold defining a gas channel, the gas manifold comprising a plurality of vectored gas ports in fluid communication with the gas channel, wherein the plurality of vectored gas ports are configured to create a curtain effect gas flow within the patient cavity to form a gas curtain within the patient cavity and adjacent to the at least one vent opening.

In certain embodiments, a ventilation mask is disclosed that comprises a mask body defining a patient cavity, the mask body comprising: a patient opening in fluid communication with the patient cavity; and at least one vent opening formed through the mask body, the at least one vent opening in fluid communication with the patient cavity, wherein the at least one vent opening is disposed generally opposite to the patient opening; at least one gas fence disposed adjacent to the at least one vent opening, the at least one gas fence extending axially toward the patient opening; and a gas manifold coupled to the mask body, the gas manifold defining a gas channel, the gas manifold comprising a plurality of gas ports in fluid communication with the gas channel.

In certain embodiments, a method of introducing a gas into a ventilation mask is disclosed that comprises introducing the gas into a patient cavity of the ventilation mask via a plurality of gas ports; directing the gas via the plurality of gas ports to create a curtain effect gas flow; and forming a gas curtain within the patient cavity and adjacent to at least one vent opening of the ventilation mask.

In certain embodiments, a method of introducing a gas into a ventilation mask is disclosed that comprises introducing the gas into a patient cavity of the ventilation mask via a plurality of gas ports; and receiving a sample gas flow from the patient cavity via a sampling portal.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
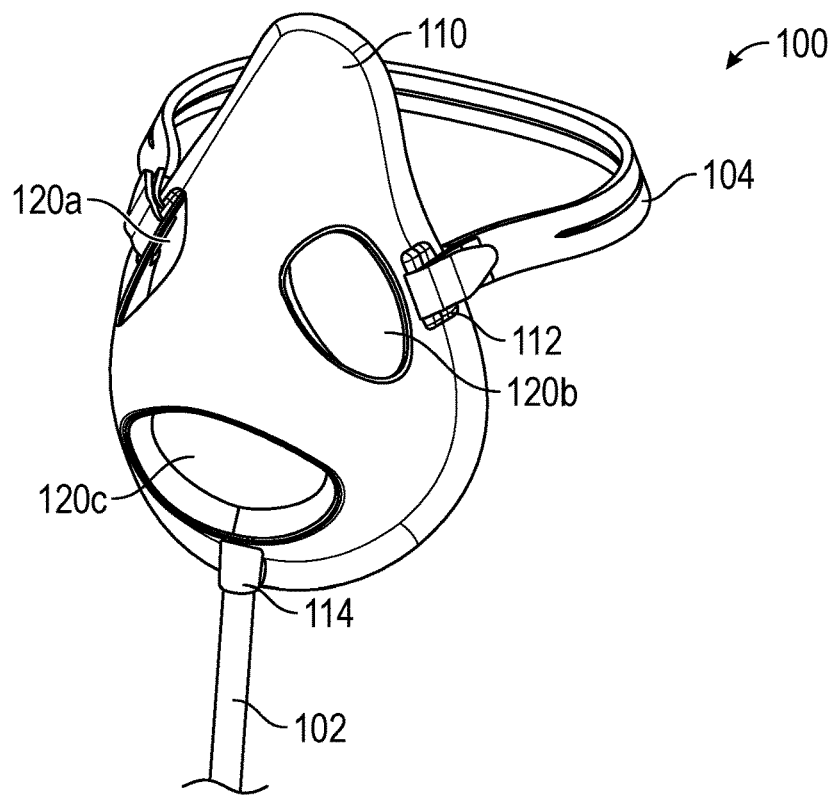
FIG. 1 is a front perspective view of an embodiment of a ventilation mask, in accordance with various aspects of the present disclosure.

The disclosed ventilation mask incorporates features to deliver oxygen or other gases to a patient with an open mask structure. The ventilation mask can utilize fluid dynamics to provide high concentrations of oxygen or other gases to the patient despite the open mask structure. Further, the ventilation mask can utilize fluid dynamics to measure or sample gases exhaled by the patient.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of supplemental gas to a patient by a medical practitioner using the disclosed ventilation mask, it is to be understood that this description is only an example of usage and does not limit the scope of the claims. Various aspects of the disclosed ventilation mask may be used in any application where it is desirable to administer and/or sample gases.

The disclosed ventilation mask overcomes several challenges discovered with respect to certain ventilation masks. One challenge with certain conventional ventilation masks is that high concentrations of oxygen or other gases cannot be administered to a patient using an open mask structure. Because delivery of high concentrations of oxygen or other gases may be required, the use of conventional ventilation masks is undesirable. Another challenge with certain conventional ventilation masks is that gases exhaled by a patient may be difficult to sample and/or measure when using an open mask structure. Because sampling or measurement of exhaled gases may be required during the administration of gases, the use of conventional ventilation masks is undesirable.

Therefore, in accordance with the present disclosure, it is advantageous to provide a ventilation mask as described herein that allows for administration of high concentrations of oxygen or other gases while permitting an open mask structure. The disclosed ventilation mask provides gas ports and/or gas fences to direct gas flow toward a patient and away from vent openings in the ventilation mask. Further, it is advantageous to provide a ventilation mask as described herein that allows for the sampling of exhaled gases while permitting an open mask structure. The disclosed ventilation mask provides gas flow that directs exhaled gases toward sampling ports within the ventilation mask.

An example of a ventilation mask that permits high concentrations of oxygen or other gases and/or sampling of exhaled gases while retaining an open mask structure is now described.

FIG. 1 is a front perspective view of a ventilation mask 100, in accordance with various aspects of the present disclosure. In the depicted example, the ventilation mask 100 can be utilized to administer oxygen or other supplemental gases to a patient. The ventilation mask 100 can direct a supplemental gas, such as oxygen, via the supply tubing 102 to the ventilation mask 100 via the supply gas port 114. As described herein, a gas manifold can distribute the supplemental gas through the mask body 110 to the patient.

As illustrated, the ventilation mask 100 can be worn by the patient over the patient's mouth and nose. The ventilation mask 100 can be attached to the patient by a strap 104 worn over the head of the patient. The strap 104 can be coupled to the mask body 110 at strap openings 112 formed in the mask body 110.

In the depicted example, the ventilation mask 100 can have a generally open mask structure. As illustrated, the mask body 110 includes one or more vent openings 120a, 120b, 120c formed therethrough. The vent openings 120a, 120b, 120c can allow for access or fluid communication with the patient cavity defined by the mask body 110. In some embodiments, the mask body 110 includes three vent openings 120a, 120b, 120c. The upper vent openings 120a, 120b can be positioned to be adjacent to a patient's nose when the ventilation mask 100 is worn. Further, the upper vent openings 120a, 120b can be laterally spaced apart on either side of the patient's nose when the ventilation mask 100 is worn. The lower vent opening 120c can be positioned to be adjacent to a patient's mouth when the ventilation mask 100 is worn.

Advantageously, by utilizing one or more vent openings 120a, 120b, 120c, the ventilation mask 100 can allow for exhaled gases such as carbon dioxide to be cleared from the patient cavity of the ventilation mask, reducing the incidence of carbon dioxide rebreathing. Further, the vent openings 120a, 120b, 120c can permit various tasks to be performed without removing the ventilation mask 100. Tasks can include, but are not limited to, medical procedures, eating, drinking, hygiene procedures, and/or talking. For example, the vent openings 120a, 120b, 120c can allow for nasal and/or oral bronchoscopy procedures, administering medications, and access for mouthpieces and/or nebulizers. Further, the open structure of the ventilation mask 100 can increase patient comfort by accommodating various facial features and reducing patient claustrophobia.

Figure 2:
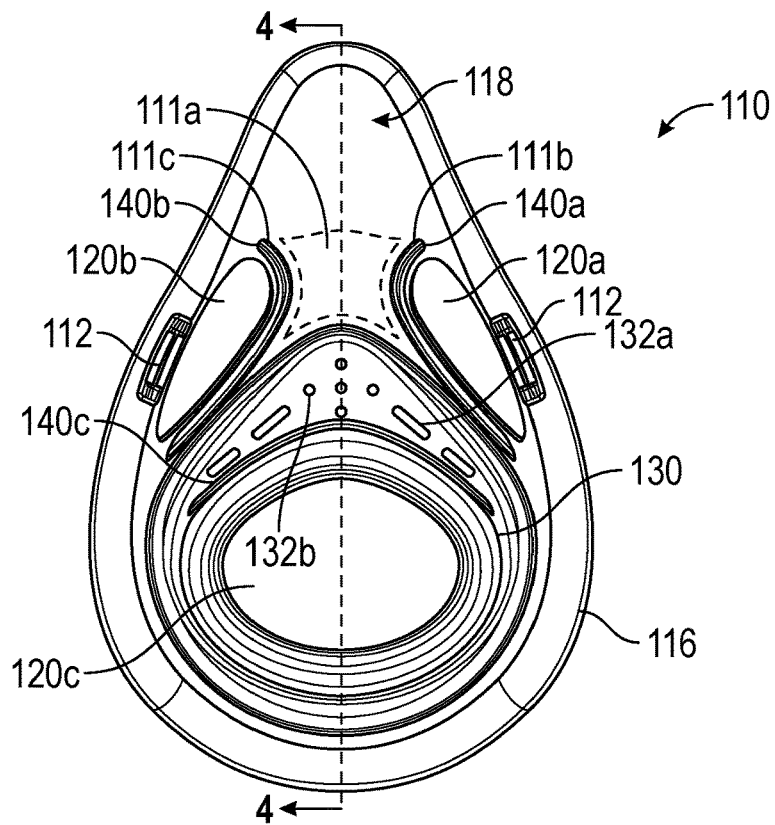
FIG. 2 is a rear elevation view of a mask body of the ventilation mask of FIG. 1, in accordance with various aspects of the present disclosure.

FIG. 2 is a rear elevation view of a mask body 110 of the ventilation mask 100 of FIG. 1, in accordance with various aspects of the present disclosure. In some applications, the mask body 110 is configured to be worn over the mouth and nose of a patient to permit supplemental gases to be administered to the patient. The patient opening 116 of the mask body 110 can engage against the patient's face. Optionally, the patient opening 116 can be in sealing engagement with the patient.

In the depicted example, the mask body 110 defines a patient cavity 118 over the patient's mouth and nose. As described herein, supplemental gases can be introduced and directed within the patient cavity 118. Further, the vent openings 120a, 120b, 120c may be in fluid communication with the patient cavity 118.

In some embodiments, the mask body 110 can be formed from a soft material, such as a polymer. The mask body 110 can be compliant to permit the mask body 110 to accommodate a wide variety of facial features.

In the depicted example, supplemental gases can be introduced into the patient cavity 118 via one or more gas ports 132a, 132b. The gas ports 132a, 132b can be formed in a gas manifold 130 disposed within the patient cavity 118 of the mask body 110.

In some applications, the gas ports 132a, 132b can administer high concentrations of supplemental gas to the patient cavity 118 and ultimately to the patient, notwithstanding the vent openings 120a, 120b, 120c in fluid communication with the patient cavity 118.

As illustrated, the gas jets or ports 132a, 132b create and direct gas flows and/or flow paths towards the nose and/or mouth of the patient and away from the vent openings 120a, 120b, 120c. In the depicted example, the gas ports 132a, 132b are vectored to direct the gas flow in a desired direction. During operation, the gas ports 132a, 132b can utilize fluid dynamic characteristics to generate "curtain effect" gas flow (e.g., a distributed flow) or a gas curtain that directs gas flow towards the patient's mouth and nose while acting as a barrier or boundary to environmental gases entering the patient cavity 118 via the vent openings 120a, 120b, 120c. In some embodiments, the boundary formed by the gas curtain can be disposed between or adjacent to the vent openings 120a, 120b, 120c and the patient's breathing anatomy, such as the patient's mouth and nose. During operation, the boundary formed by the gas flow can create a protected volume of supplemental gas while reducing mixing with ambient or environmental gases.

As shown, the gas ports 132a, 132b can include various geometric features to direct the gas flow as desired. For example, the gas ports 132a can have an elongated slot geometry, cross-section, or profile. Optionally, the gas ports 132a can further include rounded edges. In some embodiments, the gas ports 132a can be tapered to direct gas flow therethrough. For example, the gas ports 132a can be axially tapered towards the patient.

Further, the gas ports 132b can have a circular geometry, cross-section, or profile. In some embodiments, the gas ports 132b can be tapered to direct gas flow therethrough. For example, the gas ports 132b can be axially tapered towards the patient.

Additionally, in some embodiments, the gas ports 132a, 132b can be arranged to promote curtain effect gas flow and high concentrations of supplemental gas. For example, the gas ports 132a can be disposed on the gas manifold 130 generally circumferentially around an upper edge of the vent opening 120c. Further, the gas ports 132b can be clustered together on the gas manifold 130 at an upper edge of the vent opening 120c. In some embodiments of the present disclosure, any of the gas ports 132a and gas ports 132b can positioned between the vent openings 120a, 120b, 120c. In some embodiments, the gas ports 132b can be positioned between or flanked by the gas ports 132a. Optionally, the gas ports 132a, 132b can be configured to follow the shape of a patient's upper lip region to the corners of the patient's mouth.

Advantageously, the arrangement and geometric features of the gas ports 132a, 132b can provide the curtain effect gas flow described herein. By utilizing the directed gas flow provided by the gas ports 132a, 132b, supplemental gas can be directed to patients with varying facial features and without the use of a snorkel or other structure that extends into the patient cavity, proximal to the patient when the ventilation mask 100 is worn.

The gas ports 132b can have a diameter of between approximately 0.01 inches to 0.1 inches. In some embodiments, the gas ports 132b comprise a diameter of approximately 0.062 inches. In some embodiments, adjacent gas ports 132b are spaced apart between approximately 0.1 inches to 0.75 inches. In some embodiments, adjacent gas ports 132b are spaced apart in a first direction approximately 0.1 inches, and adjacent gas ports 132b are spaced apart in a second direction, different than the first direction, approximately 0.2 inches. In some embodiments elongate gas ports 132a comprise a length of between approximately 0.13 to 0.75 inches, and a width of between approximately 0.01 to 0.15 inches. In some embodiments, a first gas port 132a has a length of approximately 0.26 inches and a second gas port has a length of approximately 0.3 inches.

Optionally, the mask body 110 can include one or more breath indicators 111a, 111b, 111c to provide a visual indication if a patient is breathing. For example, the breath indicators 111a, 111b, 111c can provide a visual indication in response to exhaled carbon dioxide.

In some embodiments, the breath indicators 111a, 111b, 111c are strips or patches of color changing or colorimetric media. For example, the breath indicators 111a, 111b, 111c can comprise a color changing media paper. During operation, the breath indicators 111a, 111b, 111c can undergo a reaction in the presence of carbon dioxide, which causes a change color in the breath indicators 111a, 111b, 111c.

In some embodiments, the breath indicators 111a, 111b, 111c can present a blue color in the absence of carbon dioxide and present a yellow color in the presence of carbon dioxide. Advantageously, the breath indicators 111a, 111b, 111c can rapidly respond to the presence of carbon dioxide to allow the breath indicators 111a, 111b, 111c to change color on a breath by breath basis (e.g. cycle between blue to yellow with each breath, or cycle between transparent and opaque with each breath). Further, by changing color in response to a patient's breath, the breath indicators 111a, 111b, 111c can visually indicate if a patient is breathing or carbon dioxide buildup within the patient cavity 118 from a distance.

In some embodiments, the breath indicators 111a, 111b, 111c are disposed about the mask body 110 at regions that are exposed to the exhaled breath of the patient. As illustrated, the breath indicators 111a, 111b, 111c can receive the exhaled breath of the patient from the patient's nose and/or mouth. For example, a breath indicator 111a can be disposed close to a patient's nose between gas fences 140a, 140b. Further, in some embodiments, breath indicators 111b, 111c can be disposed on gas fences 140a, 140b respectively. Advantageously, embodiments of the ventilation mask described herein allow for the breath indicators 111a, 111b, 111c to signal a patient's breathing at supplemental gas flow rates ranging from 0 to 1, 2, 3, 4, 5, 8, 10, 12, 14, 16, 18, or 20 liters per minute.

Optionally, the breath indicators 111a, 111b, 111c can comprise a paper-based indicator. The breath indicators 111a, 111b, 111c can be affixed or coupled to the mask body 110 with a secondary structure. In some embodiments, the breath indicators 111a, 111b, 111c can be bonded to an interior surface of the mask body 110. Optionally, the breath indicators 111a, 111b, 111c can be over-molded into the mask body 110. In some embodiments, the breath indicators 111a, 111b, 111c can be seen through the mask body 110 by a caretaker or clinician.

Advantageously, by providing breath indicators 111a, 111b, 111c, caregivers and clinicians can readily determine if a patient is breathing, as chest wall motion may be insufficient and other indicators, such as pulse oximetry, may be lagging indicators. In some applications, breath indicators 111a, 111b, 111c can provide clinicians timely warnings of respiratory conditions.

Figure 3:
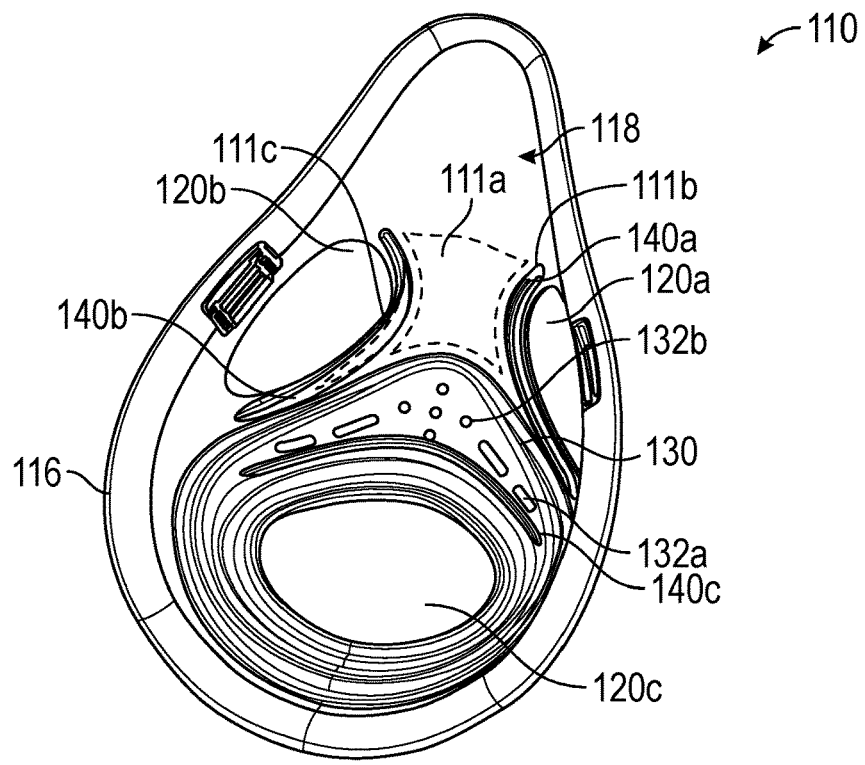
FIG. 3 is a rear perspective view of the mask body of FIG. 2, in accordance with various aspects of the present disclosure.

FIG. 3 is a perspective view of the mask body 110 of FIG. 2, in accordance with various aspects of the present disclosure. With reference to FIGS. 2 and 3, the gas fences 140a, 140b, 140c extending from the mask body 110 and/or the gas manifold 130 can help control and/or direct supplemental gas flow from the gas ports 132a, 132b. Further, the gas fences 140a, 140b, 140c can promote the curtain effect gas flow of the supplemental gas as well as prevent entrainment of environmental air into the patient cavity 118.

In the depicted example, the gas fences 140a, 140b, 140c can extend axially within the patient cavity 118 toward the patient opening 116 or the patient generally. The gas fences 140a, 140b, 140c can extend axially while maintaining space for a patient's facial features and for patient comfort. Further, the edges of the gas fences 140a, 140b, 140c can be rounded for patient comfort.

The gas fences 140a, 140b, 140c can be disposed generally between the gas ports 132a, 132b and the vent openings 120a, 120b, 120c. In the depicted example, the gas fences 140a, 140b, 140c are disposed proximal to the gas ports 132a, 132b. In some applications, the relative location of the gas fences 140a, 140b, 140c with respect to the gas ports 132a, 132b creates a barrier to promote maintaining the gas curtain near the nose and mouth of the patient. Further, relative location the gas fences 140a, 140b, 140c relative to the vent openings 120a, 120b, 120c creates a barrier to prevent the entrainment of environmental gases into the supplemental gas flow and into the patient cavity 118 generally.

As illustrated, the gas fences 140a, 140b, 140c can be curved to follow the profile of the vent openings 120a, 120b, 120c, respectively. The gas fences 140a, 140b, 140c can follow along an outer edge of the vent openings 120a, 120b, 120c. In some embodiments, the gas fences 140a, 140b, 140c can extend along a portion of the vent openings 120a, 120b, 120c to provide an open mask structure to the mask body 110.

For example, the gas fences 140a, 140b, 140c can extend at least partially circumferentially along an edge of the vent openings 120a, 120b, 120c. In some embodiments, the gas fences 140a, 140b, 140c can be positioned between the vent openings 120a, 120b, 120c. In some applications, the gas fences 140a, 140b can be disposed on either side of the patient's nose and the gas fence 140c can be disposed below the patient's nose to promote curtain effect gas flow and to maintain supplemental gas concentration in the area adjacent to the patient's nose and mouth while preventing or limiting the entrainment of environmental gases from the vent openings 120a, 120b, 120c. Further, in some embodiments, the lower gas fence 140c can promote curtain effect gas flow around the lower vent opening 120c to promote supplemental gas concentration in the area adjacent to the patient's mouth.

Figure 4:
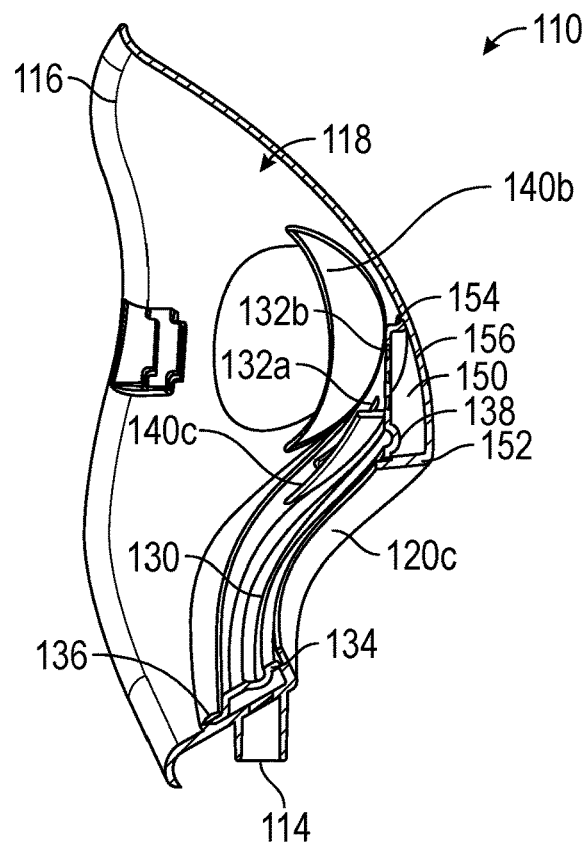
FIG. 4 is a cross-sectional view of the mask body of FIG. 2 taken along section line 4-4, in accordance with various aspects of the present disclosure.

FIG. 4 is a cross-sectional view of the mask body 110 of FIG. 2 taken along section line 4-4, in accordance with various aspects of the present disclosure. As illustrated, the supplemental gas channel 150 directs supplemental gas from the supply gas port 114 to the gas ports 132a, 132b formed through the gas manifold 130. In some embodiments, the supplemental gas channel 150 directs supplemental gas from the supply gas port 114 around the lower vent opening 120c. Optionally, the supplemental gas channel 150 can be circumferentially disposed around the lower vent opening 120c.

In the depicted embodiment, the supplemental gas channel 150 is defined by the gas manifold 130 disposed against the mask body 110. For example, an inner edge 134 and an outer edge 136 of the gas manifold 130 can engage with an inner lip 152 and an outer lip 154 of the mask body 110 to define the supplemental gas channel 150. In particular, the inner edge 134 of the gas manifold 130 can engage with the inner lip 152 of the mask body 110 and the outer edge 136 of the gas manifold 130 can engage with the outer lip 154 of the mask body 110. Further, a manifold surface 138 of the gas manifold 130 and a mask surface 156 of the mask body 110 can cooperate and be spaced apart to define the walls of the supplemental gas channel 150.

Figure 5:
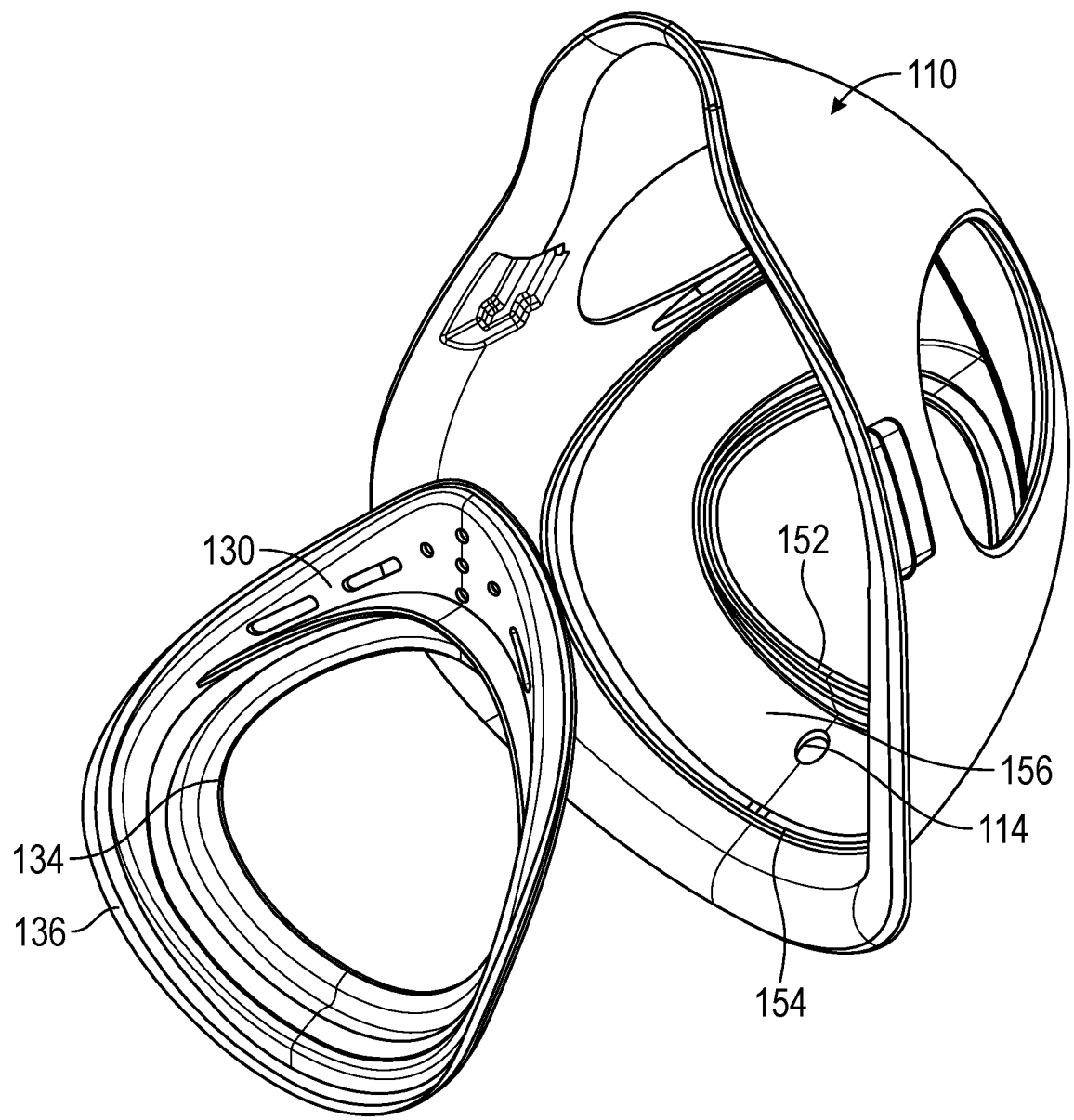
FIG. 5 is an exploded view of the gas manifold and the mask body of FIG. 2, in accordance with various aspects of the present disclosure.

FIG. 5 is an exploded view of the gas manifold 130 and the mask body 110 of FIG. 2, in accordance with various aspects of the present disclosure. As described herein, the gas manifold 130 and the mask body 110 can cooperatively define the supplemental gas channel 150. In the depicted embodiment, the mask body 110 can include features that are complimentary to the features of the gas manifold 130 to receive and engage the gas manifold 130 to the mask body 110 and define the supplemental gas channel 150 therein.

For example, the inner lip 152 and the outer lip 154 of the mask body 110 can define an engagement profile for the gas manifold 130. The inner edge 134 and the outer edge 136 of the gas manifold 130 can be located with the engagement profile formed by the inner lip 152 and the outer lip 154. In some embodiments, the engagement profile of the mask body 110 can allow the gas manifold 130 to be aligned with the mask body 110 to allow the supplemental gas channel 150 to be formed. In some embodiments, the mask body 110 and/or the gas manifold 130 can include alignment posts, holes, or other features to align the gas manifold 130 with the mask body 110.

In the depicted example, the gas manifold 130 can have a complimentary shape to nest within the mask body 110. In some embodiments, the gas manifold 130 is disposed with the inner portion of the mask body 110. Optionally, the gas manifold 130 can be disposed along an outer portion of the mask body 110 to define a supplemental gas channel 150 along an outer surface of the mask body 110.

In some embodiments, the gas manifold 130 can be resiliently or elastically engaged to the mask body 110, wherein portions of the mask body 110 and/or the gas manifold 130 resiliently deform to couple the gas manifold 130 to the mask body 110.

Upon engagement, the gas manifold 130 can be sealingly engaged with the mask body 110 to prevent leakage of the supplemental gas flow through the supplemental gas channel 150. In some embodiments, the gas manifold 130 can be bonded to the mask body 110 with any suitable adhesive (e.g. solvent bonding, adhesive bonding). In some embodiments, the gas manifold 130 can be welded to the mask body 110, such as by laser or RF welding using high frequency electromagnetic energy to fuse the materials. In some embodiments, the gas manifold 130 and the mask body 110 are mechanically coupled, such as by using a latch, an interference fit, or heat staking. The gas manifold 130 and the mask body 110 can be formed from similar materials or different materials.

Figure 6:
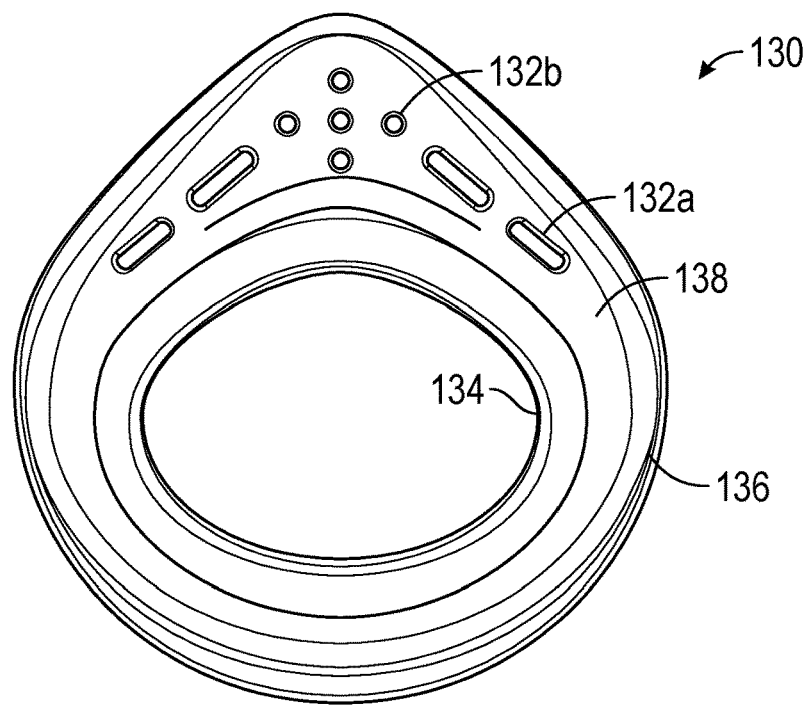
FIG. 6 is a front elevation view of the gas manifold of FIG. 2, in accordance with various aspects of the present disclosure.

FIG. 6 is a front elevation view of the gas manifold 130 of FIG. 2, in accordance with various aspects of the present disclosure. In the depicted embodiment, the gas manifold 130 defines the inner portion of the supplemental gas channel 150 (as shown in FIG. 4). As illustrated, the gas manifold 130 can have a generally modified toroidal shape.

Further, the manifold surface 138 can define the inner wall of the supplemental gas channel 150. As illustrated, the gas ports 132a, 132b can be formed through the manifold surface 138 to allow fluid communication with the supplemental gas channel 150. The manifold surface 138 can extend between the inner edge 134 and the outer edge 136 of the gas manifold 130. As illustrated, the inner edge 134 of the gas manifold 130 can be formed around a lower vent opening 120c of the mask body 110.

Figure 7:
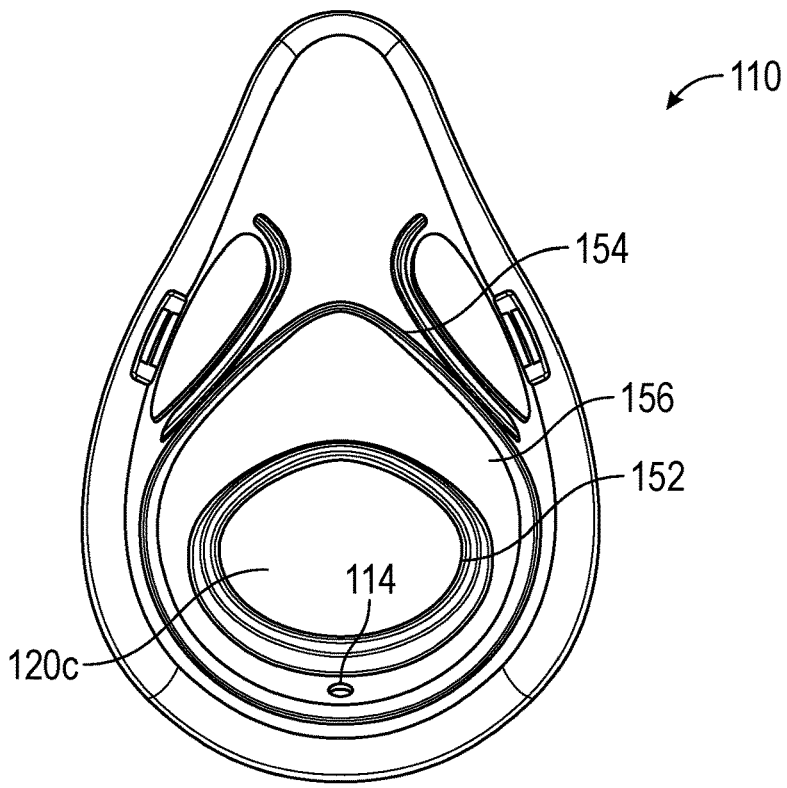
FIG. 7 is a rear elevation view of the mask body of FIG. 2, in accordance with various aspects of the present disclosure.

FIG. 7 is a rear elevation view of the mask body 110 of FIG. 2, in accordance with various aspects of the present disclosure. In the depicted embodiment, the mask body 110 defines the outer portion of the supplemental gas channel 150 (as shown in FIG. 4). As illustrated, the mask body 110 can have a generally modified conical shape or any other anatomically suitable shape.

As illustrated, the mask surface 156 can define the outer wall of the supplemental gas channel 150. In some embodiments, the supply gas port 114 can be formed through the mask surface 156 to allow fluid communication with the supplemental gas channel 150. The mask surface 156 can be defined between the spaced apart inner lip 152 and the outer lip 154 of the mask body 110. Optionally, the inner lip 152 and the outer lip 154 can extend axially toward the patient or the gas manifold 130 to provide engagement features for the gas manifold 130 to engage with. As illustrated, the inner lip 152 can be circumferentially formed around the lower vent opening 120c of the mask body 110.

As described herein, embodiments of the ventilation mask allow for effective and efficient delivery and administration of supplemental gases to the patient while retaining an open mask structure. Advantageously, embodiments of the present disclosure do not require gas delivery or sampling structures that protrude through the patient cavity of the mask to a position near the patient's nose or mouth. The absence of gas delivery or sampling structures near the patient's nose or mouth can prevent unintended contact between the mask and the patient, provide increased volume in the mask for facial features, and can provide consistent performance for a variety of patient facial structures and breathing types (e.g., mouth and/or nose breathing). Further, features of the embodiment of the ventilation mask described herein prevent the loss of supplemental gas to the environment and prevent the entrainment of environmental gases into the supplemental gas flow.

Figure 8:
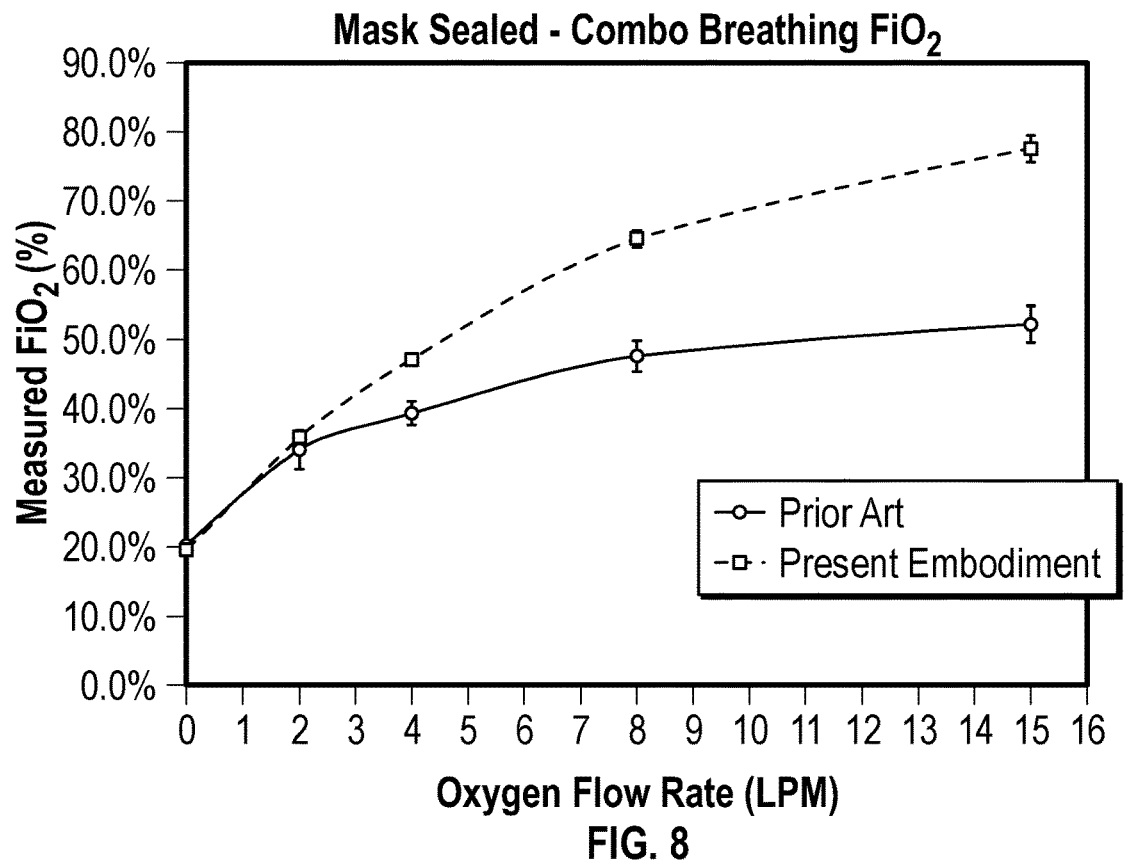
FIG. 8 is a chart depicting a fraction of inspired oxygen compared to an oxygen flow rate for a ventilation mask in accordance with various aspects of the present disclosure.
Figure 9:
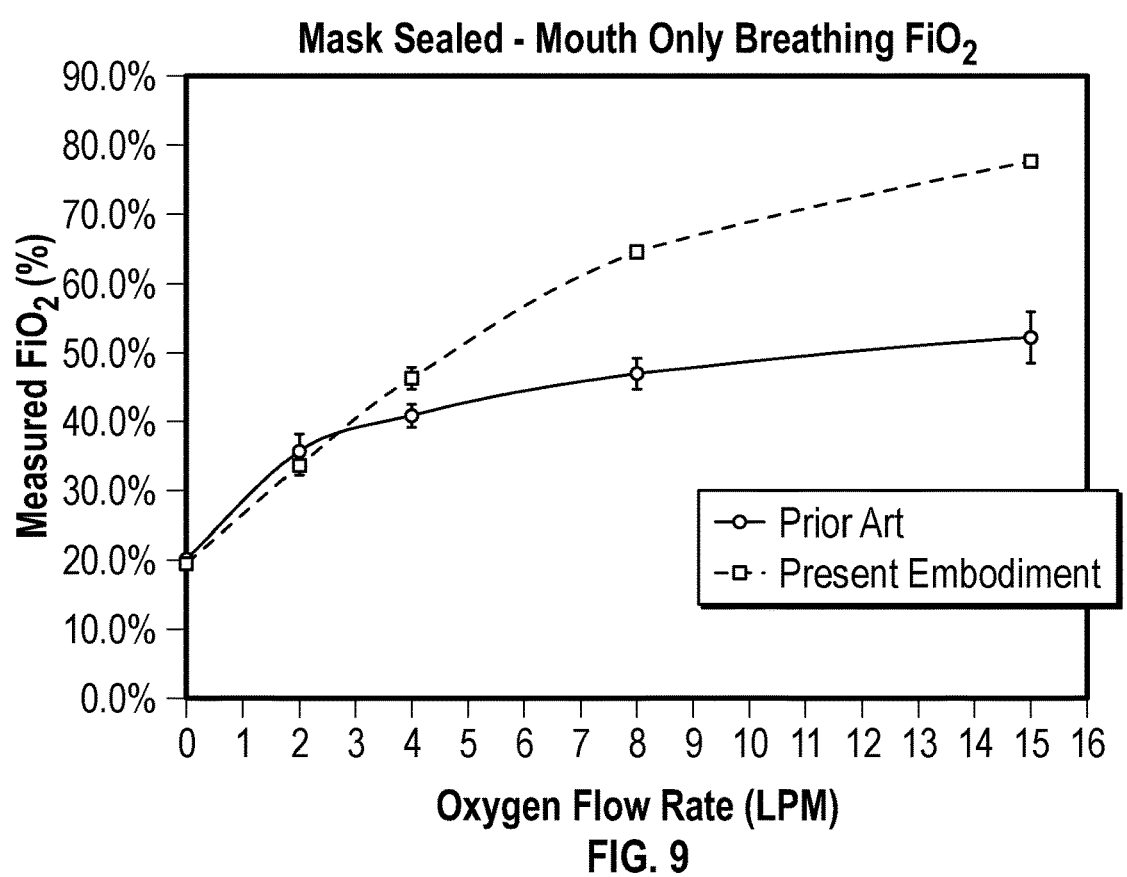
FIG. 9 is a chart depicting a fraction of inspired oxygen compared to an oxygen flow rate for a ventilation mask in accordance with various aspects of the present disclosure.
Figure 10:
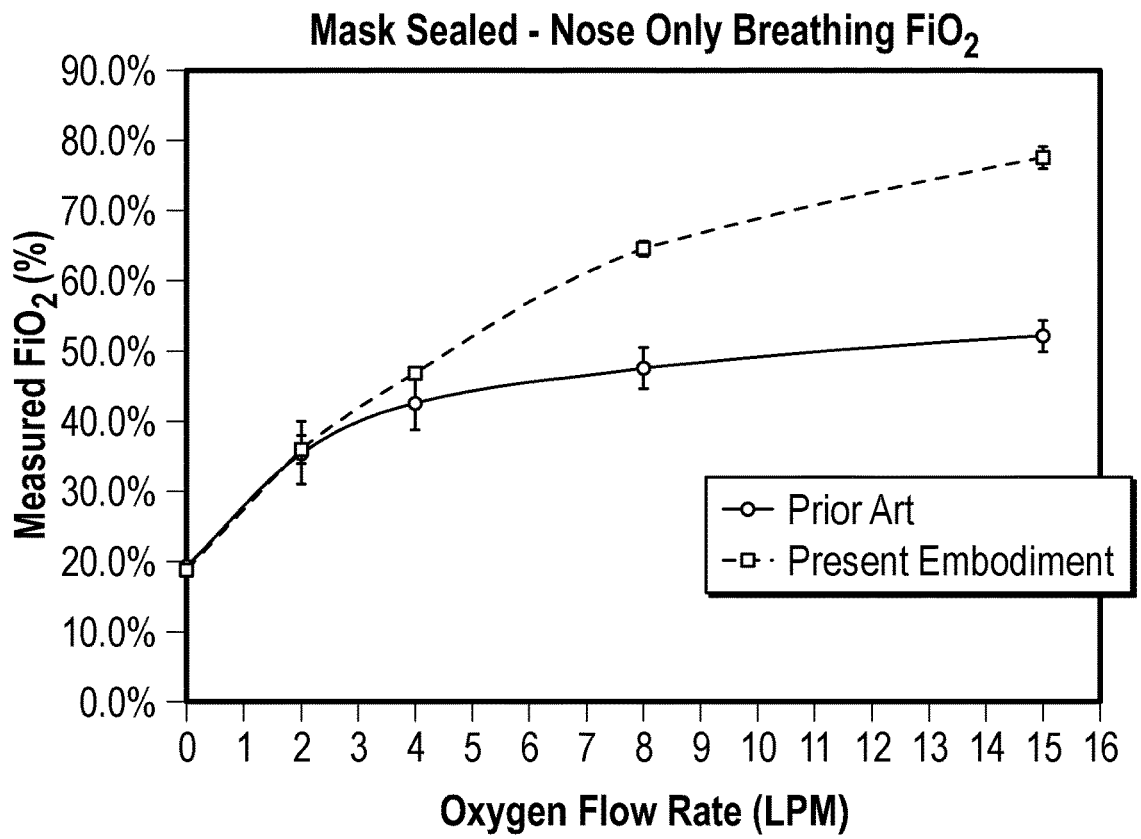
FIG. 10 is a chart depicting a fraction of inspired oxygen compared to an oxygen flow rate for a ventilation mask in accordance with various aspects of the present disclosure.

FIG. 8 is a chart depicting a fraction of inspired oxygen compared to an oxygen flow rate for a ventilation mask in accordance with various aspects of the present disclosure. Embodiments of the ventilation mask have been tested using a breathing simulator with a tidal volume of 500 mL per inspiration and a respiratory rate of 15 breaths per minute. During simulation, breathing through a combination of the nose and mouth was simulated. FIG. 9 is a chart depicting a fraction of inspired oxygen compared to an oxygen flow rate for a ventilation mask in accordance with various aspects of the present disclosure. During simulation, breathing through the mouth was simulated. FIG. 10 is a chart depicting a fraction of inspired oxygen compared to an oxygen flow rate for a ventilation mask in accordance with various aspects of the present disclosure. During simulation, breathing through the nose was simulated.

With reference to FIGS. 8-10, accordingly, embodiments of the ventilation mask described herein allow for an open mask structure while providing higher concentrations of oxygen or other supplemental gases at various flow rates compared to conventional ventilation masks with an open mask structure. In some applications, the fraction of inspired oxygen provided by some embodiments of the ventilation mask described herein can range from approximately 30% to 80%. Further, as shown, at higher flow rates, embodiments of the ventilation mask described herein provide significantly higher concentrations of oxygen compared to conventional ventilation masks. For example, embodiments of the ventilation mask may effectively provide fraction of inspired oxygen rates greater than 40%, 45%, 50%, 60%, 70%, 75%, or 80%.

Advantageously, as embodiments of the ventilation mask described herein are able to deliver supplemental gas more effectively compared to conventional ventilation masks, embodiments of the ventilation mask may waste less supplemental gas during operation. For example, in some applications embodiments of the ventilation mask may waste 0% to 10%, 20%, 30%, 40%, or 50% less supplemental gas during delivery compared to conventional ventilation masks.

Figure 11:
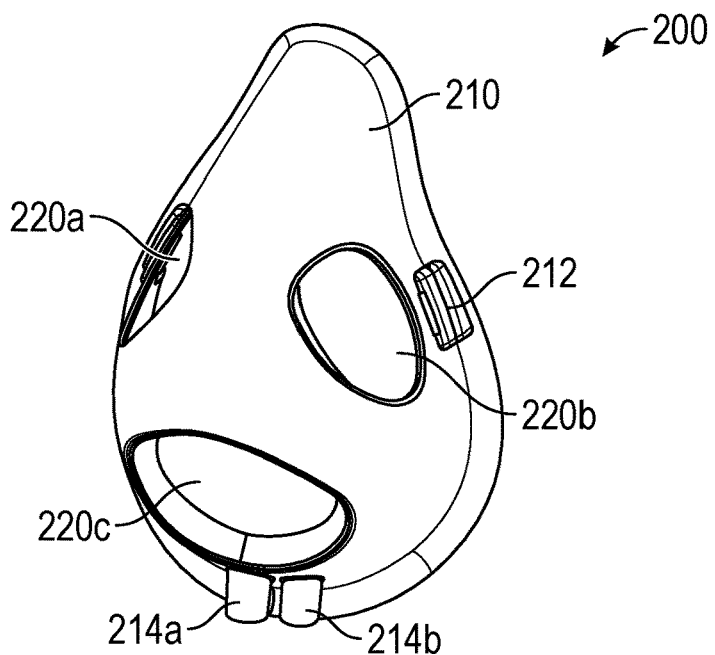
FIG. 11 is a front perspective view of another embodiment of a ventilation mask, in accordance with various aspects of the present disclosure.

FIG. 11 is perspective view of a ventilation mask 200, in accordance with various aspects of the present disclosure. In the depicted example, various features of the ventilation mask 200 may be similar to features described with respect to ventilation mask 100. Accordingly, similar reference numerals may be utilized to reference various features of ventilation mask 200 that may be similar to features of ventilation mask 100.

In the depicted example, the ventilation mask 200 can be utilized to administer supplemental gases to a patient and/or sample exhaled gases from a patient for measurement or analysis. Accordingly, in addition to directing a supplemental gas to the ventilation mask 200 via the supply gas port 214a, the ventilation mask 200 can direct exhaled gases from a patient to a monitor via a sensing port 214b. In some embodiments, multiple monitors can be connected to the sensing port 214b via pigtail connections or other suitable connections to monitor multiple parameters or for redundancy.

In some applications, capnography methods can be used with sampled exhaled gases from the ventilation mask 200 to monitor carbon dioxide levels. For example, sampled exhaled gases can be analyzed to monitor for a percentage of carbon dioxide in an exhaled breath or monitor a partial pressure of carbon dioxide in an exhaled breath. Optionally, values can be shown as a breath by breath waveform. In some embodiments, the sensing port 214b can be coupled to a negative pressure source to draw in exhaled gases from the patient cavity of the ventilation mask 200.

Figure 12:
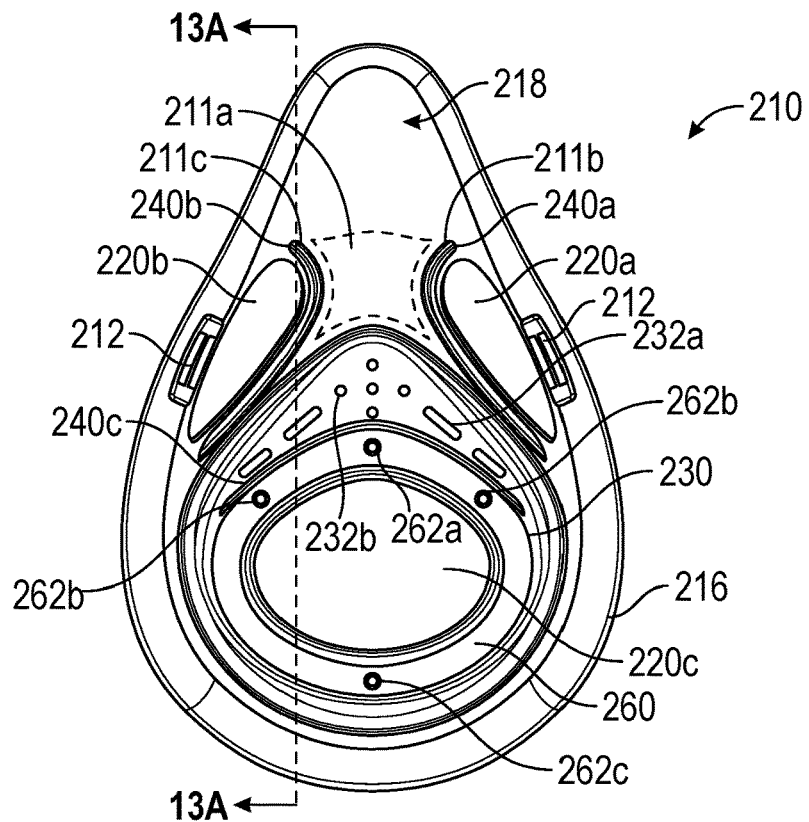
FIG. 12 is a rear elevation view of a mask body of the ventilation mask of FIG. 11, in accordance with various aspects of the present disclosure.

FIG. 12 is a rear elevation view of a mask body 210 of the ventilation mask of FIG. 11, in accordance with various aspects of the present disclosure. In some applications, the mask body 210 is configured to be worn over the mouth and nose of a patient to permit supplemental gases to be administered to a patient and to permit exhaled gases to be sampled.

In the depicted example, supplemental gases can be introduced into the patient cavity 218 via one or more gas ports 232a, 232b. In some applications, the gas ports 232a, 232b can administer high concentrations of supplemental gas to the patient cavity 218 and ultimately to the patient, notwithstanding the vent openings 220a, 220b, 220c in fluid communication with the patient cavity 218.

Optionally, exhaled gases can be sampled from the patient cavity 218 via one or more sampling portals 262a, 262b, 262c. The sampling portals 262a, 262b, 262c can be formed in a sampling cover 260 disposed within the patient cavity 218 of the mask body 210. In some embodiments, the sampling cover 260 is coupled to the gas manifold 230.

In some applications, the sampling portals 262a, 262b, 262c can intake exhaled gases from the patient cavity 218 and ultimately from the patient, notwithstanding the vent openings 220a, 220b, 220c in fluid communication with the patient cavity 218 and the gas ports 232a, 232b introducing supplemental gas flow into the patient cavity 218.

As illustrated, the sampling portals 262a, 262b, 262c can be configured to be circumferentially disposed or otherwise adjacent to a patient's mouth when the mask body 210 is worn. In the depicted embodiment, the sampling portals 262a, 262b, 262c are circumferentially disposed around the lower vent opening 220c. For example, the sampling portals 262a, 262b, 262c can be disposed circumferentially around the lower vent opening 220c at approximately 0 degrees, 60 degrees, 180 degrees, and 300 degrees from a top center portion of the vent opening 220c. As can be appreciated, the sampling portals 262a, 262b, 262c can be disposed at any circumferential position such as 0 degrees, 15 degrees, 30 degrees, 45 degrees, 60 degrees, 90 degrees, 120 degrees, 180 degrees, 210 degrees, 225 degrees, 240 degrees, 270 degrees, 300 degrees, 330 degrees, or 345 degrees. Optionally, the sampling portals 262a, 262b, 262c can be spaced apart at approximately 10 degrees, 20 degrees, 30 degrees, 45 degrees, 60 degrees, 90 degrees, 120 degrees, 135 degrees, 160 degrees, or 180 degrees. In some embodiments of the present disclosure, the sampling portals 262a, 262b, 262c can be disposed between the gas ports 232a, 232b and the vent opening 220c.

The shape and position of sampling portals 262a, 262b, 262c and/or the gas ports 232a, 232b provide for improved gas delivery and gas sampling for a variety of breathing characteristics. For example, the shape and position of sampling portals 262a, 262b, 262c and/or the gas ports 232a, 232b are configured to provide improved gas delivery and gas sampling for patients who may breathe solely or primarily from their mouth and/or nose, as well as for patients with different face morphologies and patient positions. Additionally, the shape and position of sampling portals 262a, 262b, 262c and/or the gas ports 232a, 232b are configured to facilitate providing higher fractions of inspired oxygen relative to conventional ventilation masks.

In some embodiments, the sampling portals 262a, 262b, 262c can be circular openings. Optionally, the sampling portals 262a, 262b, 262c can be any other suitable shape. The sampling portals 262a, 262b, 262c can further includes features such as hoods, scoops, and/or shrouds to promote the intake of exhaled gases and prevent the intake of supplemental gas flow or environmental gases. In some embodiments, the sampling portals 262a, 262b, 262c can range in diameter from approximately 0.02 inches to 0.1 inches.

For example, in some embodiments, sampling portals 262a, 262b, 262c can vary in size or diameter for improved functionality with patients with various breathing patterns (nose/mouth), facial features, and/or positions. Optionally, one or more sampling portals 262a, 262b, 262c can have a size or diameter that is different from other sampling portals 262a, 262b, 262c. For example, the sampling portal 262a disposed at the top center location may have a larger diameter ranging from approximately 0.04 inches to 0.07 inches, while the sampling portal 262c disposed at a bottom center location may have a smaller diameter ranging from approximately 0.02 inches to 0.04 inches. Further, in some embodiments, sampling portals 262b located at side locations may have intermediate diameters ranging from approximately 0.03 inches to 0.05 inches.

During operation, in addition to providing supplemental gas flow, the gas ports 232a, 232b can help direct exhaled gases from the patient toward the sampling portals 262a, 262b, 262c. In some embodiments, the curtain effect gas flow or gas curtain created by the gas ports 232a, 232b can create a flow path to direct the exhaled gases from the patient toward the sampling portals 262a, 262b, 262c. Advantageously, by utilizing the gas flow from the gas ports 232a, 232b, supplemental gas flow can be introduced into the patient cavity 218 while permitting sampling of exhaled gases through the sampling portals 262a, 262b, 262c, without any loss of sampling signal.

In some embodiments, gas fences 240a, 240b, 240c extending from the mask body 210 and/or the gas manifold 230 can help control and/or direct supplemental gas flow from the gas ports 232a, 232b. Further, gas fences 240a, 240b, 240c can further help control and/or direct exhaled gases toward the sampling portals 262a, 262b, 262c and prevent or limit the entrainment of environmental air into the patient cavity 218.

For example, the upper gas fences 240a, 240b can prevent or limit the entrainment of environmental gases into the patient cavity. Further, the lower gas fence 240c can be disposed generally between the gas ports 232a, 232b and at least some of the sampling portals 262a, 262b, 262c. In some applications, the relative location of the gas fence 240c with respect to the gas ports 232a, 232b and the sampling portals 262a, 262b, 262c creates a barrier to prevent or limit supplemental gas flow from entering the sampling portals 262a, 262b, 262c while promoting exhaled gases to enter the sampling portals 262a, 262b, 262c.

Optionally, the mask body 210 can include one or more breath indicators 211a, 211b, 211c to provide a visual indication if a patient is breathing.

Figure 13A:
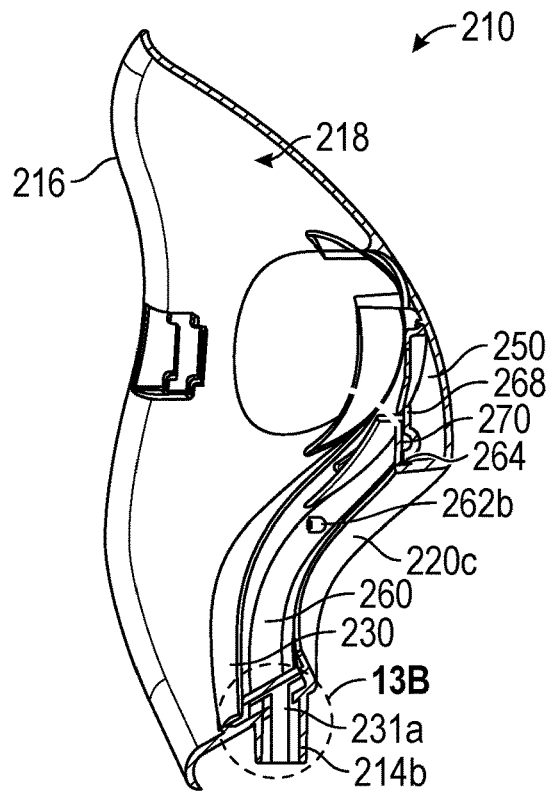
FIG. 13A is a cross-sectional view of the mask body of FIG. 12 taken along section line 13A-13A, in accordance with various aspects of the present disclosure.
Figure 13B:
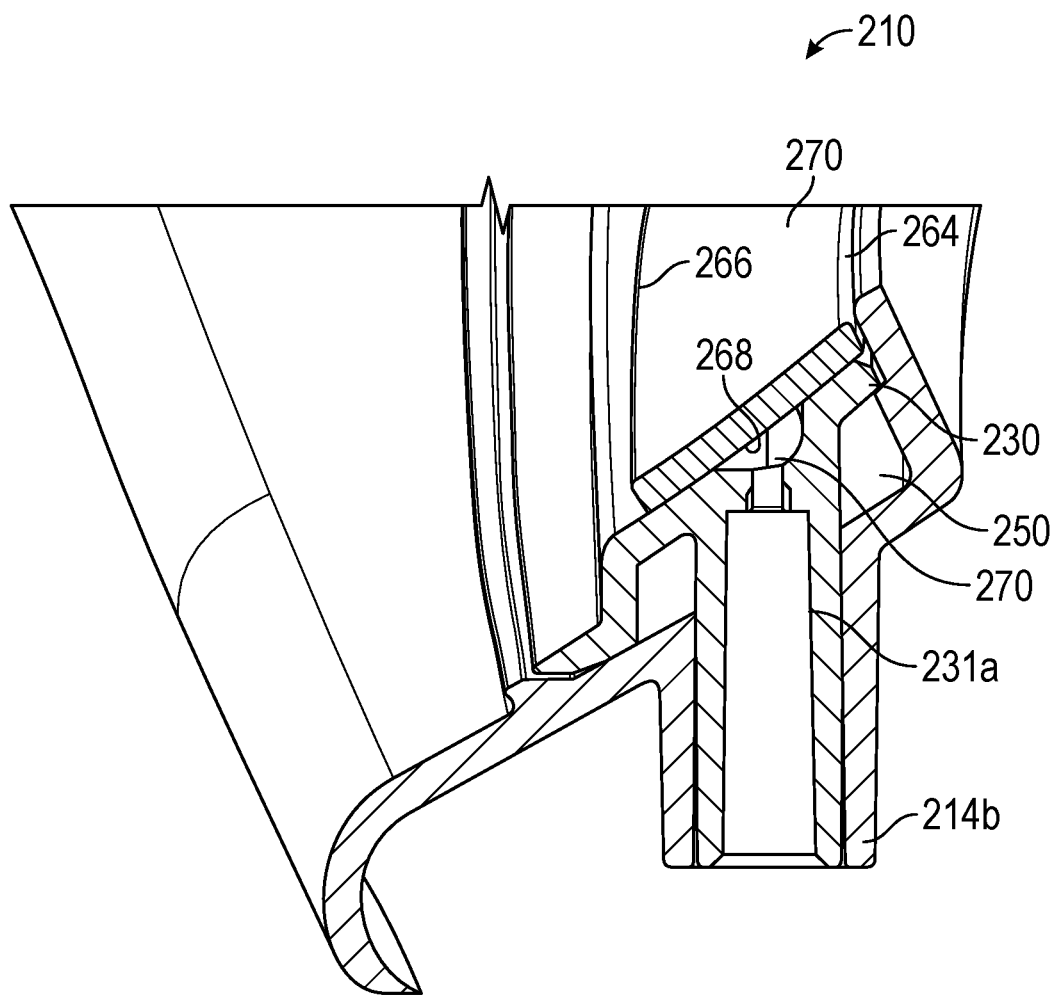
FIG. 13B is a detail view of the mask body of FIG. 13A, in accordance with various aspects of the present disclosure.

FIG. 13A is a cross-sectional view of the mask body 210 of FIG. 12 taken along section line 13A-13A, in accordance with various aspects of the present disclosure. As illustrated, the supplemental gas channel 250 directs supplemental gas from the supply gas port to the gas ports 232a, 232b formed through the gas manifold 230. Optionally, the opposite surface of the gas manifold 230 and the sampling cover 260 can form the sampling channel 270. In some embodiments, the sampling channel 270 is disposed adjacent to the gas channel 250. Optionally, the sampling channel 270 is disposed generally concentric with the gas channel 250. FIG. 13B is a detail view of the mask body 210 of FIG. 13A, in accordance with various aspects of the present disclosure. With reference to FIGS. 13A and 13B, in some embodiments, the sampling channel 270 directs exhaled gases from the sampling portals 262a, 262b, 262c to the sensing port conduit 231a. In some embodiments, the sampling channel 270 directs exhaled gases from the sampling portals 262a, 262b, 262c around the lower vent opening 220c. Optionally, the sampling channel 270 can be circumferentially disposed around the lower vent opening 220c.

In the depicted example, the sensing port conduit 231a in fluid communication with the sampling channel 270 extends from the gas manifold 230 through the gas channel 250 to direct exhaled gases out of the sampling channel 270. As illustrated, the sensing port conduit 231a can extend into and be at least partially disposed within the sensing port 214b. In some embodiments, the sensing port conduit 231a extends through the sensing port 214b.

In some embodiments, a portion of the sensing port conduit 231a can be concentrically disposed within the sensing port 214b. Optionally, the sensing port conduit 231a can have an interference or friction fit with portions of the sensing port 214b. In some embodiments, the sensing port 214b and/or the sensing port conduit 231a can be configured to be disposed below a patient's chin when the ventilation mask 200 is worn. Further, in some embodiments, the sensing port 214b and/or the sensing port conduit 231a can be configured to be disposed parallel to a patient's nose when the ventilation mask 200 is worn.

In the depicted embodiment, the sampling channel 270 is defined by the sampling cover 260 disposed against the gas manifold 230. For example, the inner edge 264 and the outer edge 266 of the sampling cover 260 can engage with an inner surface of the gas manifold 230 to define the sampling channel 270. Further, a cover surface 268 and the inner surface of the gas manifold 230 can cooperate and be spaced apart to define the walls of the sampling channel 270.

Figure 14:
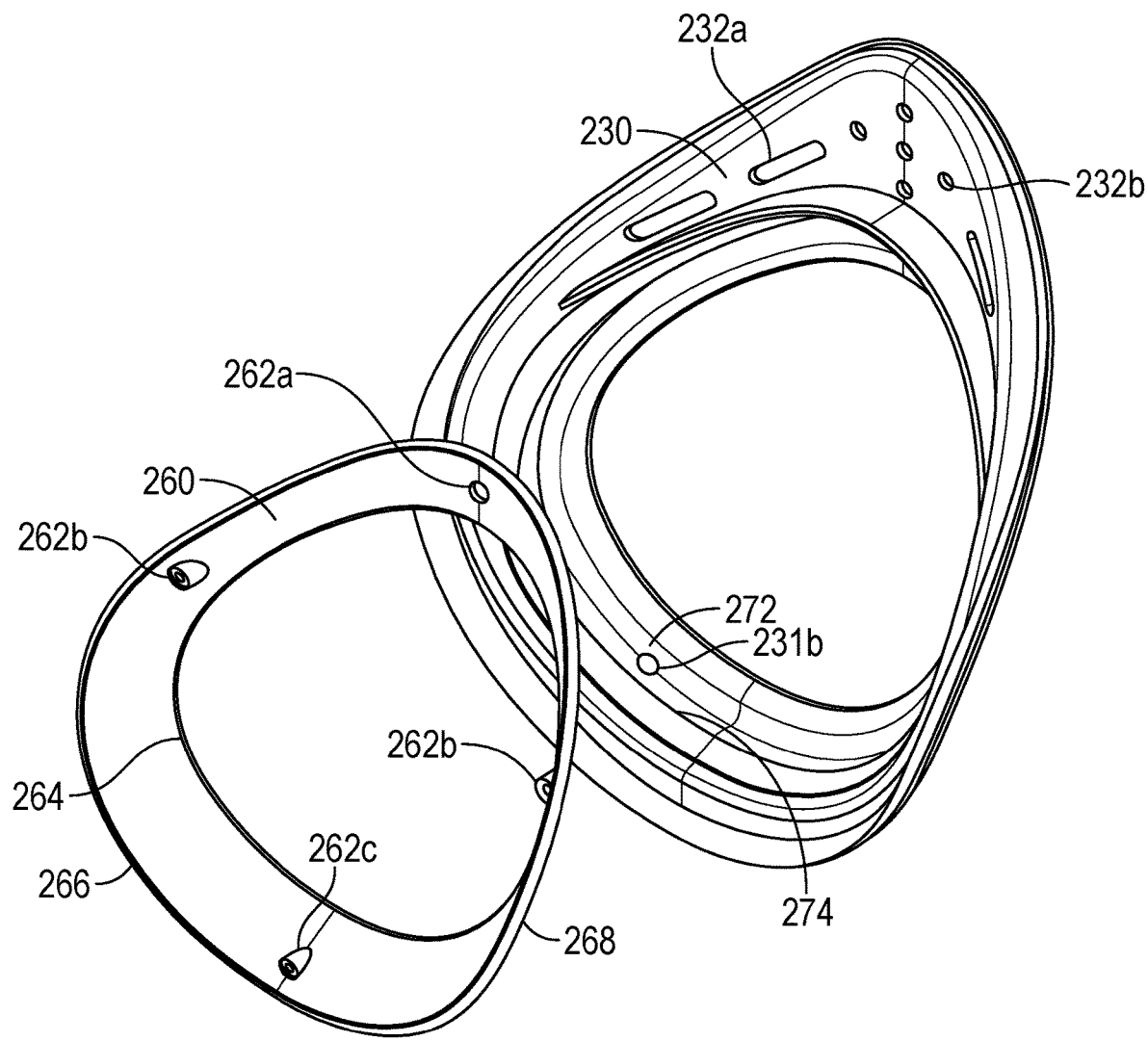
FIG. 14 is an exploded view of the sampling cover and the gas manifold of FIG. 12, in accordance with various aspects of the present disclosure.

FIG. 14 is an exploded view of the sampling cover 260 and the gas manifold 230 of FIG. 12, in accordance with various aspects of the present disclosure. As described herein, the sampling cover 260 and the gas manifold 230 can cooperatively define the sampling channel 270 therebetween. In the depicted embodiment, in addition to forming the sampling gas channel 250, the gas manifold 230 can include features that are complimentary to the features of the sampling cover 260 to receive and engage the sampling cover 260 to the gas manifold 230 and define the sampling channel 270 therein.

For example, the inner lip 272 and the outer lip 274 of the gas manifold 230 can define an engagement profile for the sampling cover 260. The inner edge 264 and the outer edge 266 of the sampling cover 260 can be located with the engagement profile formed by the inner lip 272 and the outer lip 274. In some embodiments, the engagement profile of the gas manifold 230 can allow the sampling cover 260 to be aligned with the gas manifold 230 to allow the sampling channel 270 to be formed. In some embodiments, the gas manifold 230 and/or the sampling cover 260 can include alignment posts, holes, or other features to align the sampling cover 260 with the gas manifold 230.

In the depicted example, the sampling cover 260 can have a complimentary shape to nest within the gas manifold 230. In some embodiments, the sampling cover 260 is disposed along an inner surface of the gas manifold 230. Optionally, the sampling cover 260 can be disposed along an outer surface of the gas manifold to define a sampling channel 270 along an outer surface of the gas manifold 230 or the mask body 210.

In some embodiments, the sampling cover 260 can be resiliently or elastically engaged to the gas manifold 230, wherein portions of the gas manifold 230 and/or the sampling cover 260 resiliently deform to couple the sampling cover 260 to the gas manifold 230.

Upon engagement, the sampling cover 260 can be sealingly engaged with the gas manifold 230 to prevent leakage of the exhaled gases through the sampling channel 270. In some embodiments, the sampling cover 260 can be bonded to the gas manifold 230 with any suitable adhesive (e.g. solvent bonding, adhesive bonding). In some embodiments, the sampling cover 260 can be welded to the gas manifold 230, such as by laser or RF welding using high frequency electromagnetic energy to fuse the materials. In some embodiments, the sampling cover 260 and the gas manifold 230 are mechanically coupled, such as by using a latch, an interference fit, or heat staking. The sampling cover 260 and the gas manifold 230 can be formed from similar materials or different materials.

Figure 15:
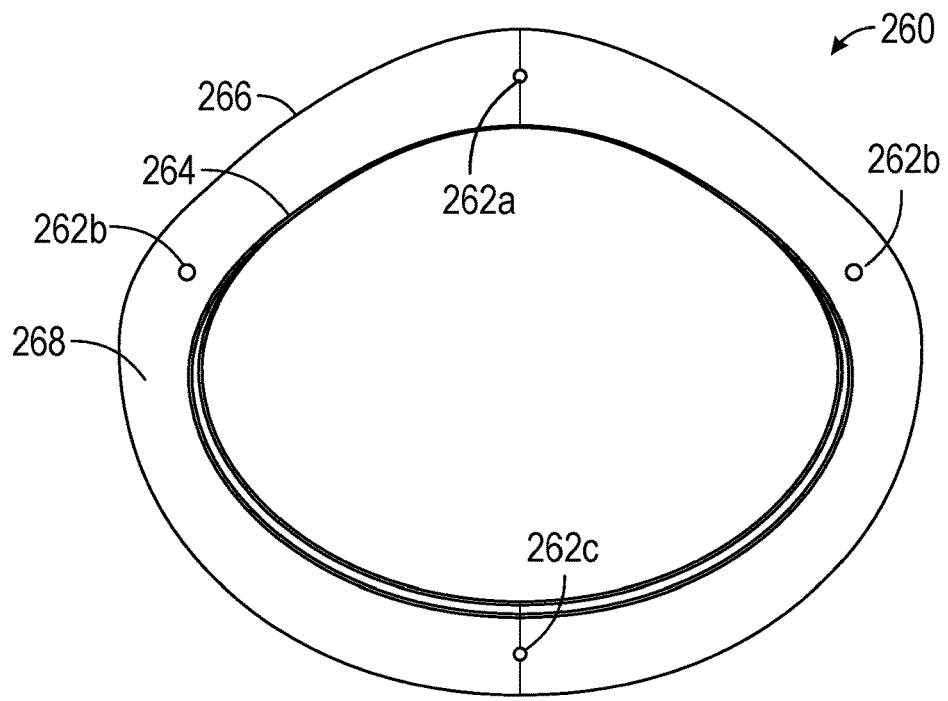
FIG. 15 is a front elevation view of the sampling cover of FIG. 12, in accordance with various aspects of the present disclosure.

FIG. 15 is a front elevation view of the sampling cover 260 of FIG. 12, in accordance with various aspects of the present disclosure. In the depicted embodiment, the sampling cover 260 defines the inner portion of the sampling channel 270. As illustrated, the sampling cover 260 can have a generally modified toroidal shape.

Further, the cover surface 268 can define the inner wall of the sampling channel 270. As illustrated, the sampling portals 262a, 262b, 262c can be formed through the cover surface 268 to allow fluid communication with the sampling channel 270. The cover surface 268 can extend between the inner edge 264 and the outer edge 266 of the sampling cover 260. As illustrated, the inner edge 264 of the sampling cover 260 can be formed around a lower vent opening 220c of the mask body 210.

Figure 16A:
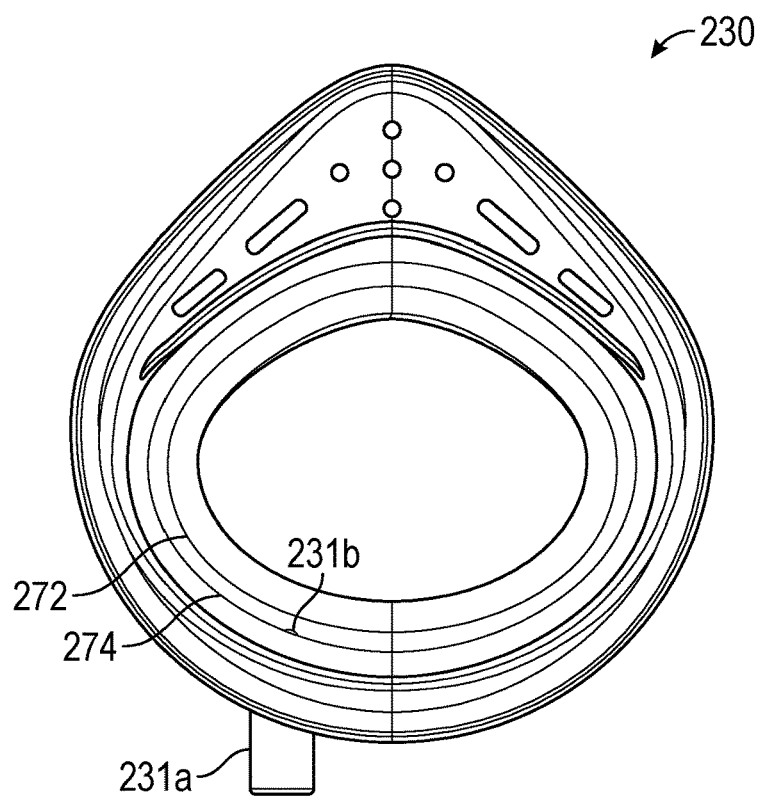
FIG. 16A is a rear elevation view of the gas manifold of FIG. 12, in accordance with various aspects of the present disclosure.

FIG. 16A is a rear elevation view of the gas manifold 230 of FIG. 12, in accordance with various aspects of the present disclosure. In the depicted embodiment, the outer surface of the gas manifold 230 defines the outer portion of the sampling channel 270.

As illustrated, the groove formed between the inner lip 272 and the outer lip 274 defines the outer portion of the sampling channel 270. In some embodiments, a conduit opening 231b for the sensing port conduit 231a can be formed through the groove formed between the inner lip 272 and the outer lip 274. The width of the groove can be defined between the spaced apart inner lip 272 and the outer lip 274 of the gas manifold 230. Optionally, the inner lip 272 and the outer lip 274 can extend axially toward the patient or the sampling cover 260 to provide engagement features for the sampling cover 260 to engage with. As illustrated, the inner lip 272 can be circumferentially formed around the lower vent opening 220c of the mask body 210.

Figure 16B:
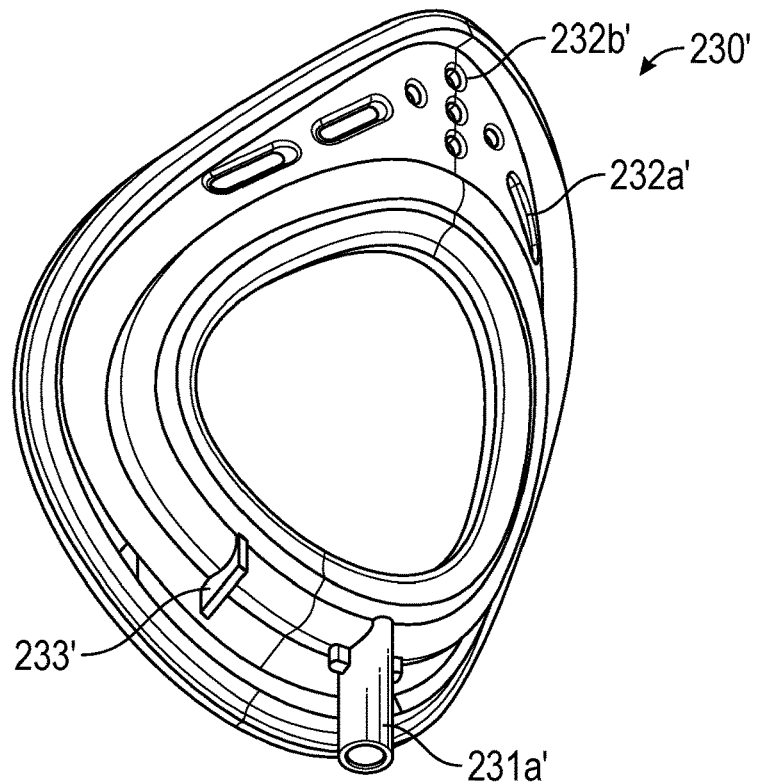
FIG. 16B is a front perspective view of the gas manifold of FIG. 16A, in accordance with various aspects of the present disclosure.
Figure 16C:
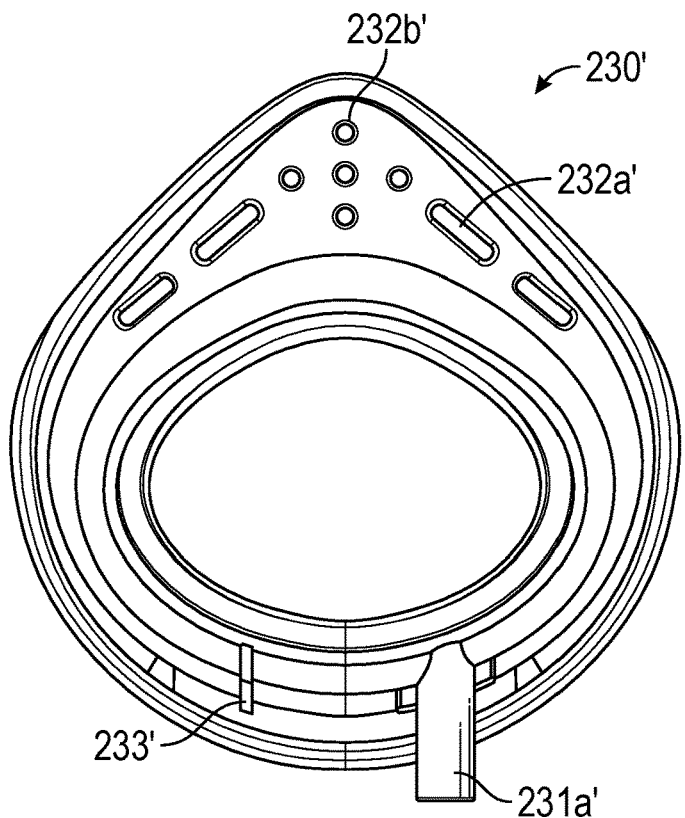
FIG. 16C is a front elevation view of the gas manifold of FIG. 16A, in accordance with various aspects of the present disclosure.

FIG. 16B is a front perspective view of another embodiment of a gas manifold 230', in accordance with various aspects of the present disclosure. FIG. 16C is a front elevation view of the gas manifold 230' of FIG. 16B, in accordance with various aspects of the present disclosure. In the depicted example, the gas manifold 230' allows for flow through the supplemental gas channel to be balanced or otherwise evenly distributed.

As described herein, the gas manifold 230' in conjunction with the mask body define a supplemental gas channel to direct supplemental gas from the supply gas port to the gas ports 232a', 232b'. In some applications, the sensing portion conduit 231a' can extend through the supplemental gas channel 250, creating a flow restriction or obstruction. In the depicted example, the gas manifold 230' includes a protrusion 233' extending at least partially into the supplemental gas channel to create a complimentary flow restriction or obstruction to balance the flow through the supplemental gas channel. As can be appreciated, the protrusion 233' can be disposed opposite to the sensing portion conduit 231'. In some embodiments, the protrusion 233' can be any suitable shape to obstruct or restrict a desired portion of the supplemental gas channel.

As described herein, embodiments of the ventilation mask described herein allow for effective sampling of a patient's exhaled gases while permitting administration of supplemental gases with an open mask structure.

Figure 17:
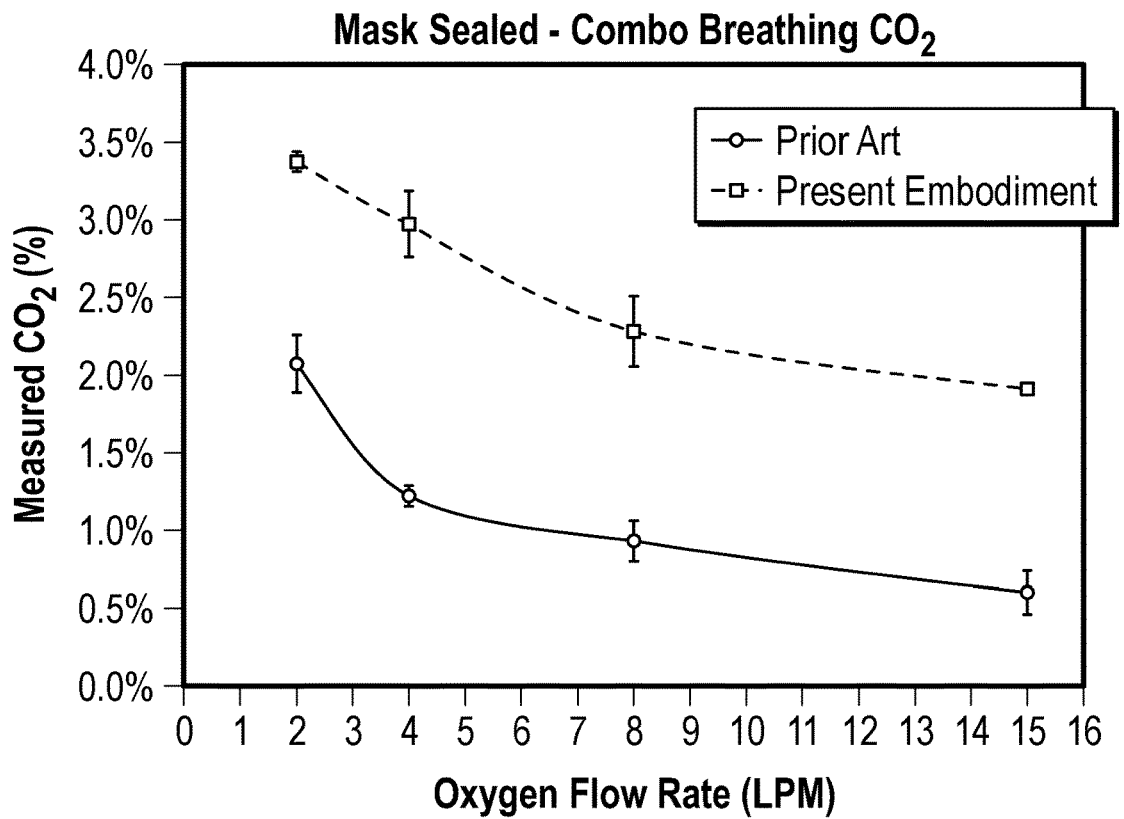
FIG. 17 is a chart depicting a measured carbon dioxide compared to an oxygen flow rate for a ventilation mask in accordance with various aspects of the present disclosure.
Figure 18:
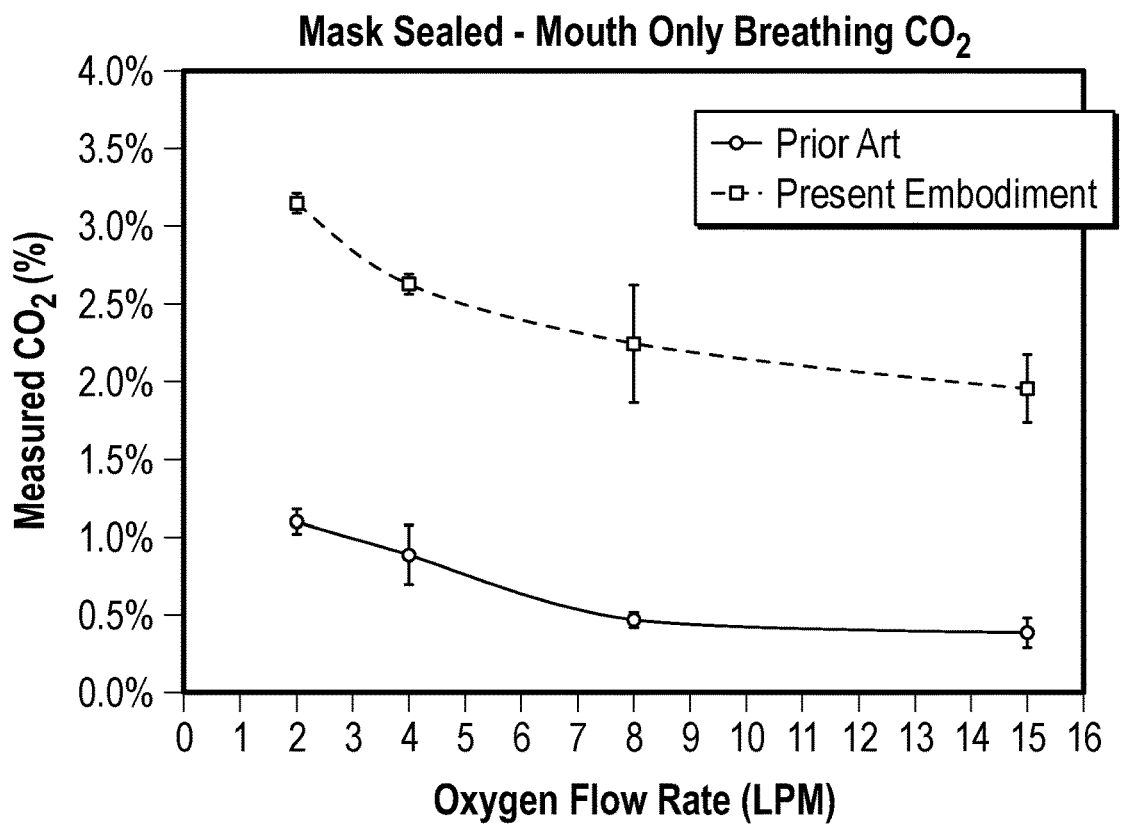
FIG. 18 is a chart depicting a measured carbon dioxide compared to an oxygen flow rate for a ventilation mask in accordance with various aspects of the present disclosure.
Figure 19:
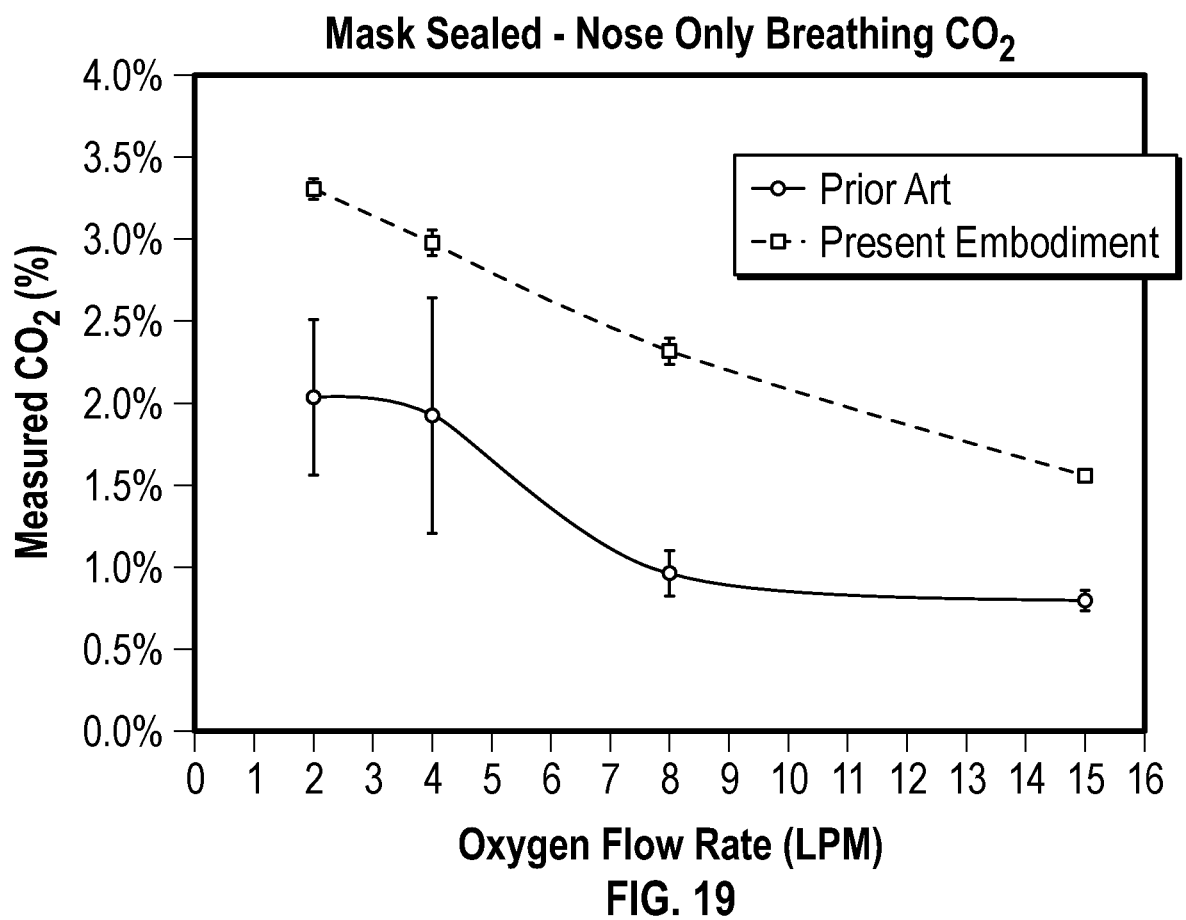
FIG. 19 is a chart depicting a measured carbon dioxide compared to an oxygen flow rate for a ventilation mask in accordance with various aspects of the present disclosure.

FIG. 17 is a chart depicting a measured carbon dioxide using capnography methods compared to an oxygen flow rate for a ventilation mask in accordance with various aspects of the present disclosure. Embodiments of the ventilation mask have been tested using a breathing simulator with a tidal volume of 500 mL per inspiration, 5% exhaled carbon dioxide and a respiratory rate of 15 breaths per minute. During simulation, breathing through a combination of the nose and mouth was simulated. FIG. 18 is a chart depicting a measured carbon dioxide using capnography methods compared to an oxygen flow rate for a ventilation mask in accordance with various aspects of the present disclosure. During simulation, breathing through the mouth was simulated. FIG. 19 is a chart depicting a measured carbon dioxide using capnography methods compared to an oxygen flow rate for a ventilation mask in accordance with various aspects of the present disclosure. During simulation, breathing through the nose was simulated.

With reference to FIGS. 17-19, accordingly, embodiments of the ventilation mask described herein allow for an open mask structure while more accurately and effectively sampling exhaled gases from a patient at various supplemental gas flow rates compared to conventional ventilation masks with an open mask structure. In some applications, the measured carbon dioxide percentage provided by some embodiments of the ventilation mask described herein can range from approximately 2% to 3.5%. Further, as shown, at higher supplemental gas flow rates, embodiments of the ventilation mask described herein provide significantly more accurate exhaled gas samples compared to conventional ventilation masks. For example, embodiments of the ventilation mask may accurately measure carbon dioxide percentages greater than 2.0%, 2.1%, 2.2%, 2.3%, 2.4%, 2.5%, 2.6%, 2.8%, 3.0%, 3.2%, 3.4%, or 3.5%.

Figure 20A:
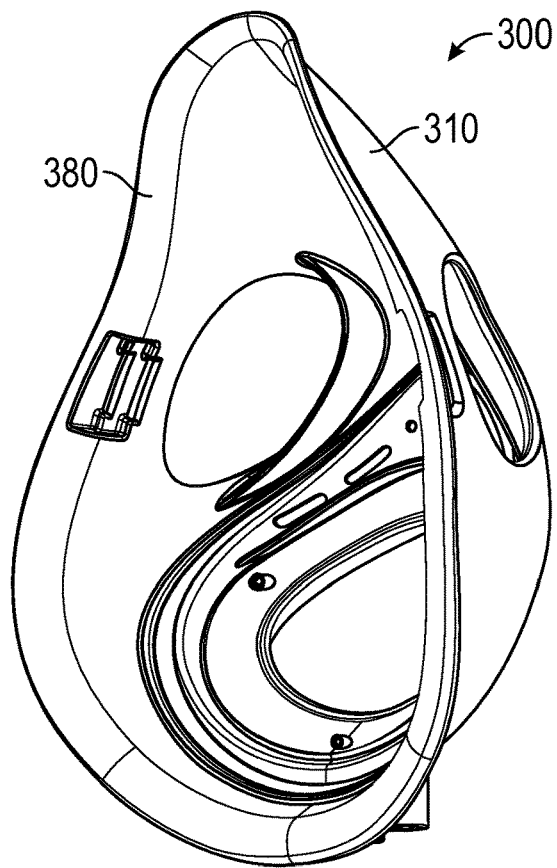
FIG. 20A is a rear perspective view of a ventilation mask, in accordance with various aspects of the present disclosure.

FIG. 20A is a rear perspective view of a ventilation mask 300, in accordance with various aspects of the present disclosure. In the depicted example, the mask body 310 can include a contact seal 380 disposed along the edge of the mask body 310 to seal the mask body 310 against a patient's facial structure. The contact seal 380 can have a resilient construction to conform and seal against the patient's facial structure. As can be appreciated, the contact seal 380 can be configured to adapt to a wide demographic of facial structures. Advantageously, by utilizing the contact seal 380, the ventilation mask 300 may be able to more effectively deliver supplemental gas flow and/or sample exhaled gases.

Figure 20B:
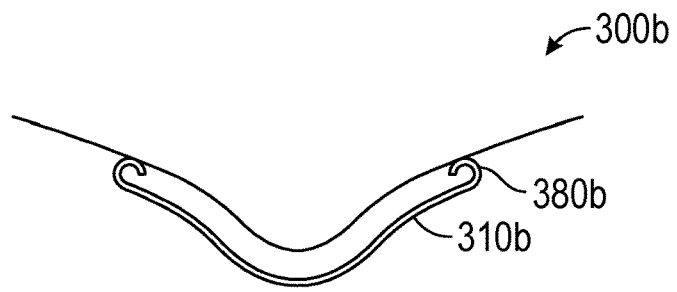
FIG. 20B is a top cross-sectional view of a ventilation mask, in accordance with various aspects of the present disclosure.

FIG. 20B is a top cross-sectional view of a ventilation mask 300b, in accordance with various aspects of the present disclosure. In the depicted example, the mask body 310b includes an inward-curling contact seal 380b. As illustrated, the edges of the contact seal 380b curl inward toward the facial structure of the patient. As can be appreciated, the curled structure of the contact seal 380b can allow for the contact seal 380b to conform to facial features of the patient. In some embodiments, the contact seal 380b can be formed from resilient materials such as thermoplastic elastomers.

Figure 20C:
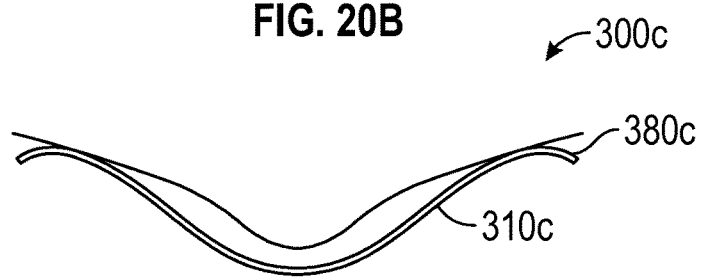
FIG. 20C is a top cross-sectional view of a ventilation mask, in accordance with various aspects of the present disclosure.

FIG. 20C is a top cross-sectional view of a ventilation mask 300c, in accordance with various aspects of the present disclosure. In the depicted example, the mask body 310c includes an outward-curling contact seal 380c. As illustrated, the edges of the contact seal 380c curl outward away from the facial structure of the patient. As can be appreciated, the curled structure of the contact seal 380c can allow for the contact seal 380c to conform to the facial features of the patient.

Figure 21:
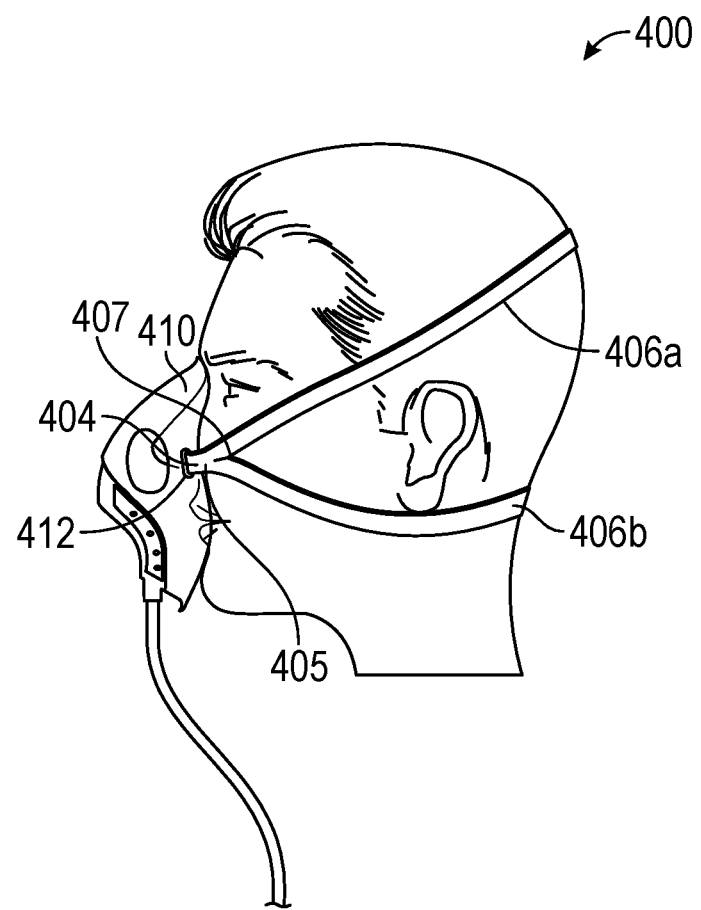
FIG. 21 is an elevation view of a ventilation mask, in accordance with various aspects of the present disclosure.

FIG. 21 is an elevation view of a ventilation mask 400, in accordance with various aspects of the present disclosure. In the depicted example, the strap 404 can be split to improve patient comfort when the ventilation mask 400 is worn over the patient's mouth and nose. As illustrated, the mask portion 405 can separate into an upper portion 406a and a lower portion 406b at a separation area 407. During operation, the upper portion 406a can be worn over a patient's ears and the lower portion 406b can be worn below a patient's ears. Advantageously, the upper portion 406a and the lower portion 406b can be separated to provide for patient comfort and proper fitting of the ventilation mask 400.

Figure 22:
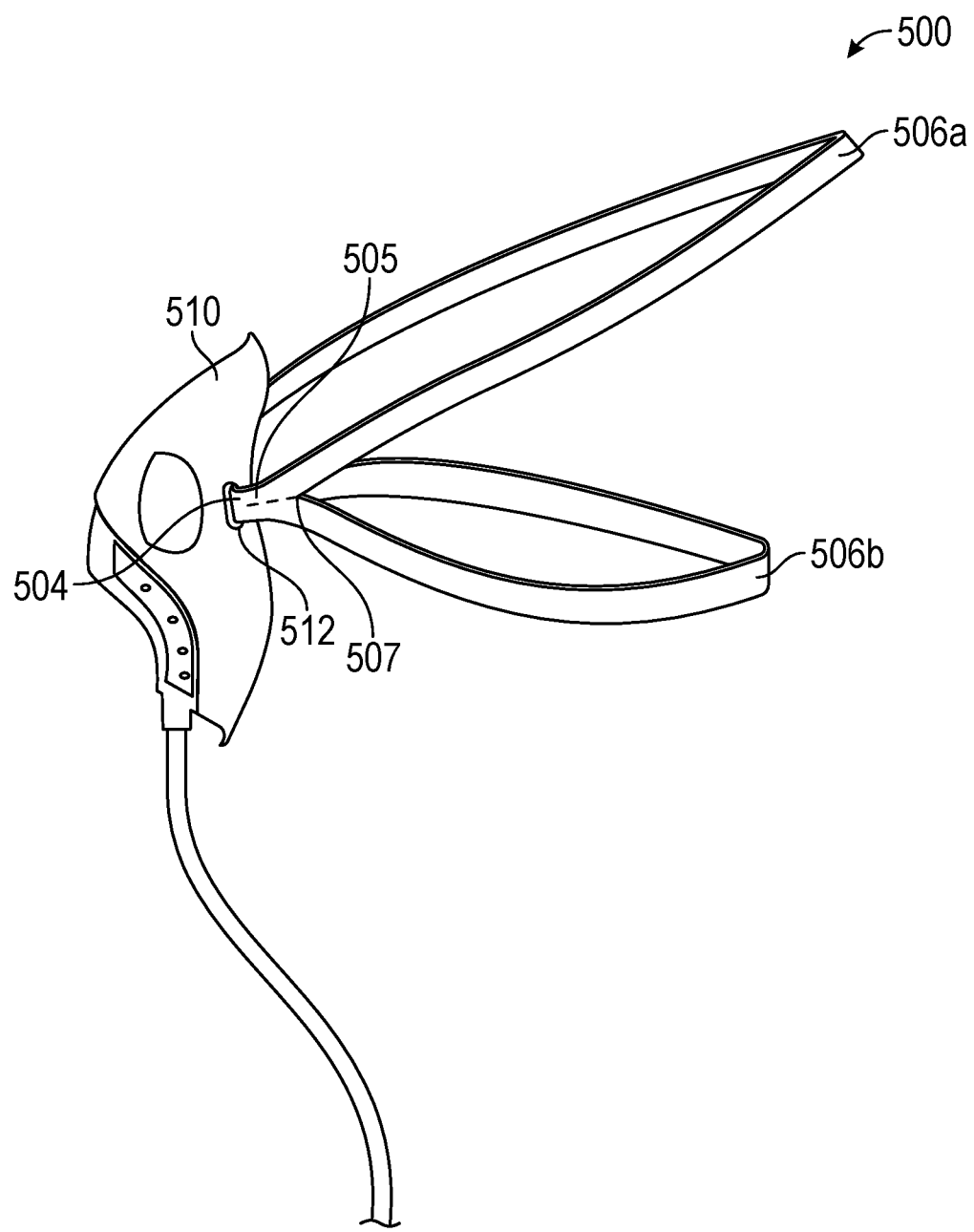
FIG. 22 is an elevation view of a ventilation mask, in accordance with various aspects of the present disclosure.

FIG. 22 is an elevation view of a ventilation mask 500, in accordance with various aspects of the present disclosure. In the depicted example, the mask portion 505 of the strap 504 can be separated by a clinician to adjust the length of the mask portion 505 and the upper and lower portions 506a, 506b of the strap 504. As illustrated, the mask portion 505 includes a perforated separation area 507 that allows the length of the upper and lower portions 506a, 506b to be extended as the mask portion 505 is separated.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A ventilation mask, comprising: a mask body defining a patient cavity, the mask body comprising: a patient opening in fluid communication with the patient cavity; and at least one vent opening formed through the mask body, the at least one vent opening in fluid communication with the patient cavity, wherein the at least one vent opening is disposed generally opposite to the patient opening; and a gas manifold coupled to the mask body, the gas manifold defining a gas channel, the gas manifold comprising a plurality of vectored gas ports in fluid communication with the gas channel, wherein the plurality of vectored gas ports are configured to create a curtain effect gas flow within the patient cavity to form a gas curtain within the patient cavity and adjacent to the at least one vent opening.

Clause 2. The ventilation mask of Clause 1, wherein at least one of the plurality of vectored gas ports comprises a tapered geometry.

Clause 3. The ventilation mask of any of Clauses 1 and 2, wherein at least one of the plurality of vectored gas ports comprises a slot cross-section.

Clause 4. The ventilation mask of any of Clauses 1-3, wherein at least one of the plurality of vectored gas ports comprises a circular cross-section.

Clause 5. The ventilation mask of any of Clauses 1-4, the mask body further comprising at least one gas fence disposed adjacent to the at least one vent opening, the at least one gas fence extending axially toward the patient opening.

Clause 6. The ventilation mask of Clause 5, wherein the at least one vent opening comprises a first and second vent openings spaced laterally apart and the at least one gas fence comprises a first gas fence adjacent to the first vent opening and a second gas fence adjacent to the second vent opening.

Clause 7. The ventilation mask of Clause 6, wherein the first gas fence extends at least partially circumferentially around the first vent opening and the second gas fence extends at least partially circumferentially around the second vent opening.

Clause 8. The ventilation mask of any of Clauses 1-4, the gas manifold further comprising at least one gas fence disposed adjacent to the at least one vent opening, the at least one gas fence extending axially toward the patient opening.

Clause 9. The ventilation mask of any of Clauses 1-4, wherein the at least one vent opening comprises a lower vent opening surrounded by the gas manifold and at least one gas fence is disposed between the lower vent opening and the plurality of vectored gas ports.

Clause 10. The ventilation mask of Clause 9, wherein the at least one gas fence extends at least partially circumferentially around the lower vent opening.

Clause 11. The ventilation mask of any of Clauses 1-10, wherein the gas manifold is disposed within the patient cavity of the mask body.

Clause 12. The ventilation mask of Clause 11, wherein the gas channel is cooperatively defined by the gas manifold and the mask body.

Clause 13. The ventilation mask of Clause 12, wherein the gas manifold is sealingly engaged with an inner surface of the mask body to define the gas channel.

Clause 14. The ventilation mask of Clause 13, wherein the inner surface of the mask body comprises a complimentary gas manifold engagement profile to engage the gas manifold and define the gas channel.

Clause 15. The ventilation mask of any of Clauses 1-10, wherein the gas manifold is disposed on an outer surface of the mask body.

Clause 16. The ventilation mask of any of Clauses 1-15, further comprising a sampling cover coupled to the gas manifold.

Clause 17. The ventilation mask of Clause 16, wherein the sampling cover defines a sampling channel, the sampling cover comprising at least one sampling portal in fluid communication with the sampling channel and the curtain effect gas flow within the patient cavity directs a sample gas flow toward the sampling portal.

Clause 18. The ventilation mask of Clause 17, wherein the at least one sampling portal is disposed adjacent to the at least one vent opening.

Clause 19. The ventilation mask of Clause 18, wherein the at least one sampling portal comprises an oxygen sampling portal and a carbon dioxide sampling portal.

Clause 20. The ventilation mask of Clause 18, wherein the at least one sampling portal comprises a hood, scoop, or shroud feature.

Clause 21. The ventilation mask of Clause 17, wherein the gas manifold comprises a sensing port conduit in fluid communication with the sampling channel, and the sensing port conduit extends through the gas channel.

Clause 22. The ventilation mask of Clause 21, wherein the gas manifold comprises a protrusion disposed opposite to the sensing port conduit and extending at least partially through the gas channel.

Clause 23. The ventilation mask of Clause 16, wherein the sampling cover is welded to the gas manifold.

Clause 24. The ventilation mask of any of Clauses 1-23, wherein the at least one vent opening comprises a lower vent opening and the gas manifold is disposed around the lower vent opening.

Clause 25. The ventilation mask of any of Clauses 1-24, further comprising a color-changing indicator coupled to the mask body, wherein the color-changing indicator is configured to change color in response to exposure to carbon dioxide.

Clause 26. The ventilation mask of Clause 25, wherein the color-changing indicator is configured to change color in response to absence of carbon dioxide.

Clause 27. The ventilation mask of Clause 25, wherein the color-changing indicator comprises a paper-based indicator.

Clause 28. The ventilation mask of Clause 25, wherein the color-changing indicator is bonded to an inner surface of the mask body or over-molded within the mask body.

Clause 29. The ventilation mask of Clause 25, wherein the color-changing indicator is disposed on a gas fence disposed adjacent to the at least one vent opening, the at least one gas fence extending axially toward the patient opening.

Clause 30. The ventilation mask of Clauses 1-29, wherein the gas manifold is welded to the mask body.

Clause 31. The ventilation mask of Clauses 1-30, wherein the mask body comprises a contact seal disposed along an edge of the mask body.

Clause 32. The ventilation mask of Clause 31, wherein the contact seal comprises an inward-curling portion or an outward-curling portion.

Clause 33. The ventilation mask of Clauses 1-32, further comprising a strap coupled to the mask body, the strap comprising: a mask portion coupled to the mask body; and an upper and lower portion extending from the mask portion.

Clause 34. The ventilation mask of Clause 33, wherein the mask portion of the strap comprises a perforated separation area configured to separate and extend a length of the upper and lower portion.

Clause 35. A ventilation mask, comprising: a mask body defining a patient cavity, the mask body comprising: a patient opening in fluid communication with the patient cavity; and at least one vent opening formed through the mask body, the at least one vent opening in fluid communication with the patient cavity, wherein the at least one vent opening is disposed generally opposite to the patient opening; at least one gas fence disposed adjacent to the at least one vent opening, the at least one gas fence extending axially toward the patient opening; and a gas manifold coupled to the mask body, the gas manifold defining a gas channel, the gas manifold comprising a plurality of gas ports in fluid communication with the gas channel.

Clause 36. The ventilation mask of Clause 35, wherein the plurality of gas ports and the at least one gas fence are configured to create a curtain effect gas flow within the patient cavity to form or retain an oxygen curtain within the patient cavity and adjacent to the at least one vent opening, the oxygen curtain comprising an oxygen concentration between 30%, 40%, 45%, 50%, 60%, 70%, 75%, or 80%.

Clause 37. The ventilation mask of Clause 35, wherein the plurality of gas ports and the at least one gas fence are configured to create a curtain effect gas flow within the patient cavity to direct the curtain effect gas flow away from the at least one vent opening.

Clause 38. The ventilation mask of any of Clauses 35-37, wherein the plurality of gas ports are configured for delivery of gas to a patient.

Clause 39. The ventilation mask of any of Clauses 35-38, wherein the at least one vent opening comprises a first and second vent openings spaced laterally apart and the at least one gas fence comprises a first gas fence adjacent to the first vent opening and a second gas fence adjacent to the second vent opening.

Clause 40. The ventilation mask of Clause 39, wherein the first gas fence extends at least partially circumferentially around the first vent opening and the second gas fence extends at least partially circumferentially around the second vent opening.

Clause 41. The ventilation mask of any of Clauses 35-40, wherein the gas channel is cooperatively defined by the gas manifold and the mask body.

Clause 42. The ventilation mask of any of Clauses 35-41, further comprising a sampling cover coupled to the gas manifold.

Clause 43. The ventilation mask of Clause 42, wherein the sampling cover defines a sampling channel, the sampling cover comprising at least one sampling portal in fluid communication with the sampling channel.

Clause 44. The ventilation mask of Clause 43, wherein the sampling channel receives a negative pressure to draw exhaled gases from the patient cavity through the at least one sampling portal.

Clause 45. The ventilation mask of Clause 43, wherein the at least one sampling portal comprises a hood, scoop, or shroud feature.

Clause 46. The ventilation mask of Clause 43, the gas manifold further comprising at least one manifold gas fence disposed adjacent to the at least one vent opening and the at least one sampling portal, the at least one manifold gas fence extending axially toward the patient opening.

Clause 47. The ventilation mask of Clause 46, wherein the at least one vent opening comprises a lower vent opening surrounded by the sampling cover and the at least one manifold gas fence is disposed between the at least one sampling portal and the plurality of vectored gas ports.

Clause 48. The ventilation mask of Clause 47, wherein the at least one manifold gas fence extends at least partially circumferentially around the lower vent opening.

Clause 49. The ventilation mask of any of Clauses 35-48, wherein the at least one vent opening comprises a lower vent opening and the gas manifold is disposed around the lower vent opening.

Clause 50. A method of introducing a gas into a ventilation mask, the method comprising: introducing the gas into a patient cavity of the ventilation mask via a plurality of gas ports; directing the gas via the plurality of gas ports to create a curtain effect gas flow; and forming a gas curtain within the patient cavity and adjacent to at least one vent opening of the ventilation mask.

Clause 51. The method of Clause 50, further comprising: directing the curtain effect gas flow away from the at least one vent opening via a gas fence disposed adjacent to the at least one vent opening.

Clause 52. The method of any of Clauses 50 and 51, further comprising: directing the gas to the plurality of gas ports via a gas channel cooperatively defined by a gas manifold and a mask body of the ventilation mask.

Clause 53. The method of Clause 50, further comprising: receiving a sample gas flow from the patient cavity via a sampling portal.

Clause 54. The method of Clause 53, further comprising: directing the sample gas flow toward the sampling portal via the curtain effect gas flow.

Clause 55. The method of Clause 53, further comprising: directing the sample gas flow toward the sampling portal via a manifold gas fence disposed on a gas manifold.

Clause 56. The method of Clause 55, further comprising: directing the curtain effect gas flow away from the sampling portal via the manifold gas fence.

Clause 57. The method of Clause 53, further comprising: measuring the sample gas flow with a carbon dioxide percentage greater than 2.0%, 2.1%, 2.2%, 2.3%, 2.4%, 2.5%, 2.6%, 2.8%, 3.0%, 3.2%, 3.4%, or 3.5%.

Clause 58. The method of Clause 50, further comprising: visually indicating exposure to carbon dioxide via a color-changing indicator coupled to the ventilation mask.

Clause 59. The method of Clause 50, further comprising: providing the gas within the patient cavity with a fraction of inspired oxygen rates greater than 40%, 45%, 50%, 60%, 70%, 75%, or 80%.

Clause 60. The method of Clause 50, further comprising: accessing the patient cavity through the at least one vent opening to perform a medical procedure.

Clause 61. The method of Clause 60, further comprising: performing a bronchoscopy procedure through the at least one vent opening.

Clause 62. A method of introducing a gas into a ventilation mask, the method comprising: introducing the gas into a patient cavity of the ventilation mask via a plurality of gas ports; receiving a sample gas flow from the patient cavity via a sampling portal; directing the gas via the plurality of gas ports to create a curtain effect gas flow; and directing the sample gas flow toward the sampling portal via the curtain effect gas flow.

Clause 63. The method of Clause 62, further comprising: directing the curtain effect gas flow away from the sampling portal via a manifold gas fence.

Clause 64. The method of Clauses 62-63, further comprising: directing the sample gas flow toward the sampling portal via a manifold gas fence disposed on a gas manifold.

Clause 65. The method of Clauses 62-64, further comprising: measuring the sample gas flow with a carbon dioxide percentage greater than 2.0%.

Clause 66. The method of Clauses 62-65, further comprising: visually indicating exposure to carbon dioxide via a color-changing indicator coupled to the ventilation mask.

Clause 67. The method of Clauses 62-66, further comprising: providing the gas within the patient cavity with a fraction of inspired oxygen rates greater than 40%.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A ventilation mask, comprising:
   a mask body defining a patient cavity, the mask body comprising:
   a patient opening in fluid communication with the patient cavity; and
   a vent opening formed through the mask body, the vent opening in fluid communication with the patient cavity, wherein the vent opening is disposed generally opposite to the patient opening; and
   a gas manifold coupled to the mask body, the gas manifold and the mask body cooperatively defining a gas channel disposed circumferentially around the vent opening, wherein a first portion of an interior surface of the gas channel is defined by the gas manifold and a second portion of the interior surface of the gas channel is defined by the mask body, the gas manifold comprising a plurality of vectored gas ports in fluid communication with the gas channel, wherein the plurality of vectored gas ports are configured to create a curtain effect gas flow within the patient cavity to form a gas curtain within the patient cavity and adjacent to the vent opening.

2. The ventilation mask of claim 1, wherein the vent opening is oriented opposite the patient's mouth when the mask is worn by a patient and at least one of the plurality of vectored gas ports comprises a geometry selected from a group consisting of a tapered geometry, a slot cross-section, and a circular cross-section which directs gas towards the patient's nose and mouth.

3. The ventilation mask of claim 2, wherein the vent opening has an upper edge, the gas manifold has an upper portion proximate the upper edge of the vent opening, and a plurality of the plurality of vectored gas ports are disposed in the upper portion of the gas manifold.

4. The ventilation mask of claim 1, wherein the gas manifold is sealingly engaged with an inner surface of the mask body to define the gas channel.

5. The ventilation mask of claim 4, wherein the inner surface of the mask body surrounds the patient cavity, further comprising an inner lip and an outer lip formed on the inner surface of the mask body, an inner lip and an outer lip formed on the gas manifold, and wherein the inner lip on the inner surface of the mask body is configured to engage the inner lip of the gas manifold and the outer lip on the inner surface of the mask body is configured to engage the outer lip of the gas manifold to secure the gas manifold to the inner surface of the mask body and form the gas channel and define the gas channel.

6. The ventilation mask of claim 1, further comprising a sampling cover coupled to the gas manifold.

7. The ventilation mask of claim 6, wherein the sampling cover defines a sampling channel, the sampling cover comprising at least one sampling portal in fluid communication with the sampling channel and the curtain effect gas flow within the patient cavity directs a sample gas flow toward the sampling portal.

8. The ventilation mask of claim 7, wherein the at least one sampling portal is disposed adjacent to the vent opening.

9. The ventilation mask of claim 8, wherein the at least one sampling portal comprises a hood, a scoop, or a shroud feature.

10. The ventilation mask of claim 7, wherein the gas manifold comprises a sensing port conduit in fluid communication with the sampling channel, and the sensing port conduit extends through the gas channel.

11. The ventilation mask of claim 10, wherein the gas manifold comprises a protrusion disposed opposite to the sensing port conduit and extending at least partially through the gas channel.

12. The ventilation mask of claim 6, wherein the sampling cover is welded to the gas manifold.

13. The ventilation mask of claim 1, wherein the vent opening comprises a lower vent opening and the gas manifold is disposed circumferentially around the lower vent opening.

14. The ventilation mask of claim 1, further comprising a color-changing indicator coupled to the mask body, wherein the color-changing indicator is configured to change color in response to exposure to carbon dioxide.

15. The ventilation mask of claim 1, wherein the gas manifold is welded to the mask body.

16. The ventilation mask of claim 1, wherein the mask body comprises a contact seal disposed along an edge of the mask body.

17. The ventilation mask of claim 16, wherein the contact seal comprises an inward-curling portion or an outward-curling portion.

18. The ventilation mask of claim 1, further comprising a strap coupled to the mask body, the strap comprising:
 a mask portion coupled to the mask body; and
 an upper and lower portion extending from the mask portion.

19. The ventilation mask of claim 18, wherein the mask portion of the strap comprises a perforated separation area configured to separate and extend a length of the upper and lower portion.

20. A ventilation mask, comprising:
 a mask body defining a patient cavity, the mask body comprising:
  a patient opening in fluid communication with the patient cavity; and
  at least one vent opening formed through the mask body, the at least one vent opening in fluid communication with the patient cavity, wherein the at least one vent opening is disposed generally opposite to the patient opening;
 at least one gas fence disposed adjacent to the at least one vent opening, the at least one gas fence extending axially toward the patient opening; and
 a gas manifold coupled to the mask body, the gas manifold and the mask body cooperatively defining a gas channel positioned circumferentially around the at least one vent opening, wherein a first portion of the gas channel is defined by the gas manifold and a second portion of the gas channel is defined by the mask body, the gas manifold comprising a plurality of gas ports positioned opposite the upper lip of a patient when the mask is worn by a patient and in fluid communication with the gas channel, wherein the plurality of gas ports and the at least one gas fence are configured to create a curtain effect gas flow within the patient cavity to form or retain an oxygen curtain within the patient cavity and adjacent to the at least one vent opening.

21. The ventilation mask of claim 20, wherein the oxygen curtain comprising an oxygen concentration between 30% and 80%.

22. The ventilation mask of claim 20, wherein the at least one vent opening comprises first and second vent openings spaced laterally apart and the at least one gas fence comprises a first gas fence adjacent to the first vent opening and a second gas fence adjacent to the second vent opening.

23. The ventilation mask of claim 22, wherein the first gas fence extends at least partially circumferentially around the first vent opening and the second gas fence extends at least partially circumferentially around the second vent opening.

* * * * *